US007635579B2

(12) United States Patent
Rayapati et al.

(10) Patent No.: US 7,635,579 B2
(45) Date of Patent: *Dec. 22, 2009

(54) METABOLIC ENGINEERING OF AMINO ACID PRODUCTION

(75) Inventors: P. John Rayapati, Decatur, IL (US); Corey M. Crafton, Decatur, IL (US)

(73) Assignee: Archer-Daniels-Midland Company, Decatur, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/978,908

(22) Filed: Oct. 30, 2007

(65) Prior Publication Data

US 2008/0090272 A1 Apr. 17, 2008

Related U.S. Application Data

(63) Continuation of application No. 11/320,139, filed on Dec. 28, 2005, now Pat. No. 7,323,321, which is a continuation of application No. 09/630,453, filed on Aug. 2, 2000, now abandoned.

(60) Provisional application No. 60/146,379, filed on Aug. 2, 1999.

(51) Int. Cl.
*C12P 13/04* (2006.01)
*C12P 13/08* (2006.01)
*C12N 15/74* (2006.01)
*C12N 1/20* (2006.01)

(52) U.S. Cl. .................. 435/106; 435/115; 435/116; 435/252.3; 435/471

(58) Field of Classification Search .................. None
See application file for complete search history.

(56) References Cited

U.S. PATENT DOCUMENTS

| | | | |
|---|---|---|---|
| 2,979,439 A | 4/1961 | Kinoshita et al. | 195/47 |
| 3,527,672 A | 9/1970 | Kubota et al. | 195/29 |
| 3,565,951 A | 2/1971 | Ishida et al. | 260/527 |
| 3,687,810 A | 8/1972 | Kurihara et al. | 195/29 |
| 3,700,557 A | 10/1972 | Nakayama et al. | 195/29 |
| 3,707,441 A | 12/1972 | Shiio et al. | 195/29 |
| 3,708,395 A | 1/1973 | Nakayama et al. | 195/29 |
| 3,825,472 A | 7/1974 | Kubota et al. | 195/29 |
| 3,970,519 A | 7/1976 | Tsuchida et al. | 195/29 |
| 4,169,763 A | 10/1979 | Nakayama et al. | 435/115 |
| 4,442,208 A | 4/1984 | Tsuchida et al. | 435/116 |
| 4,560,654 A | 12/1985 | Miwa et al. | 435/115 |
| 4,601,983 A | 7/1986 | Nakamori et al. | 435/115 |
| 4,656,135 A | 4/1987 | Tsuchida et al. | 435/116 |
| 5,118,619 A | 6/1992 | Scheer et al. | 435/116 |
| 5,188,948 A | 2/1993 | Katsurada et al. | 435/115 |
| 5,236,831 A | 8/1993 | Katsumata et al. | 435/106 |
| 5,521,074 A | 5/1996 | Katsumata et al. | 435/115 |
| 5,650,304 A | 7/1997 | Ishii et al. | 435/115 |
| 5,763,231 A | 6/1998 | Ono et al. | 435/116 |
| 5,766,925 A | 6/1998 | Sugimoto et al. | 435/252.32 |
| 5,846,790 A | 12/1998 | Kimura et al. | 435/110 |

FOREIGN PATENT DOCUMENTS

| | | |
|---|---|---|
| EP | 0 205 849 A | 12/1986 |
| EP | 0 780 476 A | 6/1997 |
| JP | 63 173592 | 7/1988 |

OTHER PUBLICATIONS

Bröer, S. and Krämer, R., "Lysine excretion by *Corynebacterium glutamicum*. 2. Energetics and mechanism of the transport system," *Eur. J. Biochem.* 202:137-143 Blackwell Sciences Ltd., Oxford, England (1991).
Bröer S. et al., "Strains of *Corynebacterium glutamicum* with Different Lysine Productivities May Have Different Lysine Excretion Systems," *Applied and Environmental Microbiology* 59:316-321 American Society for Microbiology, Washington, D.C. (1993).
Cordes, C. et al., "Cloning organization and functional analysis of *ilvA, ilvB and ilvC* genes from *Corynebacterium glutamicum*," *Gene* 112:113-116 Elsevier Science BV, Amsterdam, Netherlands (1992).
Eikmanns, B.J. et al., "Molecular aspects of lysine, threonine, and isoleucine biosynthesis in *Corynebacterium glutamicum*," Antonie van Leeuwenhoek 64:145-163 Kluwer Academic Publishers, Netherlands (1993).
Keilhauer, C. et al., "Isoleucine Synthesis in *Corynebacterium glutamicum*: Molecular Analysis of the *ilvB-ilvN-ilvC* Operon," *J. Bacteriology* 175:5595-5603 American Society for Microbiology, Washington, D.C. (1993).

(Continued)

*Primary Examiner*—Andrew Wang
*Assistant Examiner*—Kagnew H Gebreyesus
(74) *Attorney, Agent, or Firm*—Craig G. Cochenour; Duane A. Stewart, III; Buchanan Ingersoll & Rooney PC

(57) ABSTRACT

The present invention is directed towards the fermentative production of amino acids, providing microorganisms, methods and processes useful therefor. Microorganisms of the invention are capable of converting glucose to amino acids other than L-isoleucine, L-leucine and L-valine with greater efficiency than the parent strain. The efficiency of conversion may be quantified by the formula: [(g amino acid produced/g dextrose consumed)*100]=% Yield and expressed as yield from dextrose. The invention provides microorganisms that are made auxotrophic or bradytrophic for the synthesis of one or more branched chain amino acids by mutagenesis and selected for their ability to produce higher percent yields of the desired amino acid than the parental strain. Preferred microorganisms are *Corynebacterium, Brevibacterium* or *Escherichia coli* producing L-lysine. Mutagenesis is performed by classical techniques or through rDNA methodology. Methods of the invention are designed to increase the production of an amino acid by mutagenizing a parental strain, selecting cells auxotrophic or bradytrophic for the synthesis of one or more branched chain amino acids and selecting branched chain amino acid auxotrophs or bradytrophs that produce a higher percent yield from dextrose of the desired amino acid than the parental strain. Processes of the invention are designed for the production an amino acid comprising culturing in a medium a microorganism obtained by mutagenizing a parent strain to be auxotrophic or bradytrophic for branched chain amino acid synthesis and selecting variants that are capable of converting glucose to amino acids other than L-isoleucine, L-leucine and L-valine with greater efficiency than the parent strain.

10 Claims, 12 Drawing Sheets

OTHER PUBLICATIONS

Kinoshita, S. et al., "Glutamic Acid Fermentation," in *Proceedings of the International Symposium on Enzyme Chemistry*, Pan-Pacific Press, Tokyo, Japan, pp. 464-468 (1958).

Kleemann, A. et al., "Amino Acids" in *Ullmann's Encyclopedia of Industrial Chemistry*. vol. A2, Gerhartz, W. et al., eds., VCH-Verlagsgesellschaft, Weinheim, Germany, pp. 57-97 (1985).

Möckel, B. et al., "Functional and Structural Analyses of Threonine Dehydratase from *Corynebacterium glutamicum*," *J. Bacteriology 174*:8065-8072 American Society for Microbiology, Washington, D.C. (1992).

Nakayama, K. et al., "Microbial Production of Essential Amino Acids with *Corynebacterium glutamicum* mutants," in *Nutritional Improvement of Food and Feed Proteins*, Friedman, M., ed., Plenum Press, New York, NY, pp. 649-661 (1978).

Sahm, H. et al., "Construction of L-Lysine-, L-Threonine-, or L-Isoleucine-Overproducing Strains of *Corynebacterium glutamicum*," *Ann. N.Y. Acad. Sci 782*:25-39 New York Academy of Sciences, New York, NY (1996).

Van Walsem, H.J. & Thompson, M.C., "Simulated moving bed in the production of lysine," *J. Biotechnol. 59*:127-132 Elsevier Science BV, Amsterdam, Netherlands (1997).

International Search Report for International Application No. PCT/US00/20979, mailed Oct. 25, 2000.

Dialog File 351, Accession No. 7605632, Derwent WPI English language abstract for JP 63 173592.

Dialog File 351, Accession No. 11344245, Derwent WPI English language abstract for EP 0 780 476 A.

Wild-Type ILVB Nucleotide Sequence

```
         10        20        30        40
    |....|....|....|....|....|....|....|
    ggagccagaaagtcgtgaatgtggcagcttctcaacagcc  40
    cactcccgccacggttgcaagccgtggtcgatccgccgcc  80
    cctgagcggatgacaggtgcaaaggcaattgttcgatcgc  120
    tcgaggagcttaacgccgacatcgtgttcggtattcctgg  160
    tggtgcggtgctaccggtgtatgacccgctctattcctcc  200
        210       220       230       240
    |....|....|....|....|....|....|....|
    acaaaggtgcgccacgtcttggtgcgccacgagcagggcg  240
    caggccacgcagcaaccggctacgcgcaggttactggacg  280
    cgttggcgtctgcattgcaacctctggcccaggagcaacc  320
    aacttggttaccccaatcgctgatgcaaacttggactccg  360
    ttcccatggttgccatcaccggccaggtcggaagtggcct  400
        410       420       430       440
    |....|....|....|....|....|....|....|
    gctgggtaccgacgctttccaggaagccgatatccgcggc  440
    atcaccatgccagtgaccaagcacaacttcatggtcacca  480
    accctaacgacattccacaggcattggctgaggcattcca  520
    cctcgcgattactggtcgccctggccctgttctggtggat  560
    attcctaaggatgtccagaacgctgaattggatttcgtct  600
        610       620       630       640
    |....|....|....|....|....|....|....|
    ggccaccaaagatcgacctgccaggctaccgcccagtttc  640
    aacaccacatgctcgccagatcgagcaggcagtcaagctg  680
    atcggtgaggccaagaagcccgtcctttacgttggtggtg  720
    gcgtaatcaaggctgacgcacacgaagagcttcgtgcgtt  760
    cgctgagtacaccggcatcccagttgtcaccaccttgatg  800
```

Figure 2A

Wild Type ILVB Nucleotide Sequence

```
                810       820       830       840
      ....|....|....|....|....|....|....|....|
      gctttgggtactttcccagagtctcacgagctgcacatgg  840
      gtatgccaggcatgcatggcactgtgtccgctgttggtgc  880
      actgcagcgcagcgacctgctgattgctatcggctcccgc  920
      ttgatgaccgcgtcaccggtgacgttgacaccttcgcgc   960
      ctgacgccaagatcattcacgccgacattgatcctgccga  1000
               1010      1020      1030      1040
      ....|....|....|....|....|....|....|....|
      aatcggcaagatcaagcaggttgaggttccaatcgtgggc  1040
      gatgcccgcgaagttcttgctcgtctgctggaaaccacca  1080
      aggcaagcaaggcagagaccgaggacatctccgagtgggt  1120
      tgactacctcaagggcctcaaggcacgtttcccgcgtggc  1160
      tacgacgagcagccaggcgatctgctggcaccacagtttg  1200
               1210      1220      1230      1240
      ....|....|....|....|....|....|....|....|
      tcattgaaaccctgtccaaggaagttggccccgacgcaat  1240
      ttactgcgccggcgttggccagcaccaaatgtgggcagct  1280
      cagttcgttgactttgaaaagccacgcacctggctcaact  1320
      ccggtggactgggcaccatgggctacgcagttcctgcggc  1360
      ccttggagcaaaggctggcgcacctgacaaggaagtctgg  1400
               1410      1420      1430      1440
      ....|....|....|....|....|....|....|....|
      gctatcgacggcgacggctgtttccagatgaccaaccagg  1440
      aactcaccaccgccgcagttgaaggtttccccattaagat  1480
      cgcactaatcaacaacggaaacctgggcatggttcgccaa  1520
      tggcagacccctattctatgaaggacggtactcaaatacta  1560
      aacttcgtaaccagggcgagtacatgcccgactttgttac  1600
               1610      1620      1630      1640
      ....|....|....|....|....|....|....|....|
      cctttctgagggacttggctgtgttgccatccgcgtcacc  1640
      aaagcggaggaagtactgccagccatccaaaaggctcgag  1680
      agatcaacgaccgccagtagtcatcgacttcatcgtcgg   1720
      tgaagacgcacaggtatggccaatggtgtctgctggatca  1760
      tccaactccgatatccagtacgcactcggattgcgcccat  1800
                1810     1820      1830      1840
      ....|....|....|....|....|....|....|....|
      tctttgatggtgatgaatctgcagcagaagatcctgccga  1840
      cattcacgaagccgtcagcgacattgatgccgccgttgaa  1880
      tcgaccgaggcataa  1895
```

Figure 2B

Wild-Type ILVB Amino Acid Sequence

```
          10        20        30        40
 ....|....|....|....|....|....|....|....|
MNVAASQQPTPATVASRGRSAAPERMTGAKAIVRSLEELN    40
ADIVFGIPGGAVLPVYDPLYSSTKVRHVLVRHEQGAGHAA    80
TGYAQVTGRVGVCIATSGPGATNLVTPIADANLDSVPMVA   120
ITGQVGSGLLGTDAFQEADIRGITMPVTKHNFMVTNPNDI   160
PQALAEAFHLAITGRPGPVLVDIPKDVQNAELDFVWPPKI   200
         210       220       230       240
 ....|....|....|....|....|....|....|....|
DLPGYRPVSTPHARQIEQAVKLIGEAKKPVLYVGGGVIKA   240
DAHEELRAFAEYTGIPVVTTLMALGTFPESHELHMGMPGM   280
HGTVSAVGALQRSDLLIAIGSRFDDRVTGDVDTFAPDAKI   320
IHADIDPAEIGKIKQVEVPIVGDAREVLARLLETTKASKA   360
ETEDISEWVDYLKGLKARFPRGYDEQPGDLLAPQFVIETL   400
         410       420       430       440
 ....|....|....|....|....|....|....|....|
SKEVGPDAIYCAGVGQHQMWAAQFVDFEKPRTWLNSGGLG   440
TMGYAVPAALGAKAGAPDKEVWAIDGDGCFQMTNQELTTA   480
AVEGFPIKIALINNGNLGMVRQWQTLFYEGRYSNTKLRNQ   520
GEYMPDFVTLSEGLGCVAIRVTKAEEVLPAIQKAREINDR   560
PVVIDFIVGEDAQVWPMVSAGSSNSDIQYALGLRPFFDGD   600
         610       620       630       640
 ....|....|....|....|....|....|....|....|
ESAAEDPADIHEAVSDIDAAVESTEA   627
```

Figure 2C

AL203Δ nucleotide sequence.

```
              10        20        30        40
     ....|....|....|....|....|....|....|....|
     ggagccagaaagtcgtgaatgtggcagcttctcaacagcc  40
     cactcccgccacggttgcaagccgtggtcgatccgccgcc  80
     cctgagcggatgacaggtgcaaaggcaattgttcgatcgc  120
     tcgaggagcttaacgccgacatcgtgttcggtattcctgg  160
     tggtgcggtgctaccggtgtatgacccgctctattcctcc  200
             210       220       230       240
     ....|....|....|....|....|....|....|....|
     acaaaggtgcgccacgtcttggtgcgccacgagcagggcg  240
     caggccacgcagcaaccggctacgcgcaggttactggacg  280
     cgttggcgtctgcattgcaacctctggcccaggagcaacc  320
     aacttggttaccccaatcgctgatgcaaacttggactccg  360
     ttccatggttgccatcaccggccaggtcggaagtggcct  400
             410       420       430       440
     ....|....|....|....|....|....|....|....|
     gctgggtaccgacgctttccaggaagccgatatccgcggc  440
     atcaccatgccagtgaccaagcacaacttcatggtcacca  480
     accctaacgacattccacaggcattggctgaggcattcca  520
     cctcgcgattactggtcgccctggccctgttctggtggat  560
     attcctaaggatgtccagaacgctgaattggatttcgtct  600
             610       620       630       640
     ....|....|....|....|....|....|....|....|
     ggccaccaaagatcgacctgccaggctaccgcccagtttc  640
     aacaccacatgctcgccagatcgagcaggcagtcaagctg  680
     atcggtgaggccaagaagcccgtcctttacgttggtggtg  720
     gcgtaatcaaggctgacgcacacgaagagcttcgtgcgtt  760
     cgctgagtacaccggcatcccagttgtcaccaccttgatg  800
```

Figure 3 A

AL 203 A Nucleotide SEQUENCE

```
           810       820       830       840
      ....|....|....|....|....|....|....|....
      gctttgggtactttcccagagtctcacgagctgcacatgg   840
      gtatgccaggcatgcatggcactgtgtccgctgttggtgc   880
      actgcagcgcagcgacctgctgattgctatcggctcccgc   920
      tttgatgaccgcgtcaccggtgacgttgacaccttcgcgc   960
      ctgacgccaagatcattcacgccgacattgatcctgccga  1000
           1010      1020      1030      1040
      ....|....|....|....|....|....|....|....
      aatcggcaagatcaagcaggttgaggttccaatcgtgggc  1040
      gatgcccgcgaagttcttgctcgtctgctggaaaccacca  1080
      aggcaagcaaggcagagaccgaggacatctccgagtgggt  1120
      tgactacctcaagggcctcaaggcacgtttcccgcgtggc  1160
      tacgacgagcagccaggcgatctgctggcaccacagtttg  1200
           1210      1220      1230      1240
      ....|....|....|....|....|....|....|....
      tcattgaaaccctgtctgagggacttggctgtgttgccat  1240
      ccgcgtcaccaaagcggaggaagtactgccagccatccaa  1280
      aaggctcgagagatcaacgaccgcccagtagtcatcgact  1320
      tcatcgtcggtgaagacgcacaggtatggccaatggtgtc  1360
      tgctggatcatccaactccgatatccgtacgcactcgga   1400
           1410      1420      1430      1440
      ....|....|....|....|....|....|....|....
      ttgcgcccattctttgatggtgatgaatctgcagcagaag  1440
      atcctgccgacattcacgaagccgtcagcgacattgatgc  1480
      cgccgttgaatcgaccgaggcataa                 1505
```

Figure 3 B

AL203A Amino Acid SEQUENCE

```
          10         20         30         40
  ....|....|....|....|....|....|....|....|
MNVAASQQPTPATVASRGRSAAPERMTGAKAIVRSLEELN     40
ADIVFGIPGGAVLPVYDPLYSSTKVRHVLVRHEQGAGHAA     80
TGYAQVTGRVGVCIATSGPGATNLVTPIADANLDSVPMVA    120
ITGQVGSGLLGTDAFQEADIRGITMPVTKHNFMVTNPNDI    160
PQALAEAFHLAITGRPGPVLVDIPKDVQNAELDFVWPPKI    200
         210        220        230        240
  ....|....|....|....|....|....|....|....|
DLPGYRPVSTPHARQIEQAVKLIGEAKKPVLYVGGGVIKA    240
DAHEELRAFAEYTGIPVVTTLMALGTFPESHELHMGMPGM    280
HGTVSAVGALQRSDLLIAIGSRFDDRVTGDVDTFAPDAKI    320
IHADIDPAEIGKIKQVEVPIVGDAREVLARLLETTKASKA    360
ETEDISEWVDYLKGLKARFPRGYDEQPGDLLAPQFVIETL    400
         410        420        430        440
  ....|....|....|....|....|....|....|....|
SEGLGCVAIRVTKAEEVLPAIQKAREINDRPVVIDFIVGE    440
DAQVWPMVSAGSSNSDIQYALGLRPFFDGDESAAEDPADI    480
HEAVSDIDAAVESTEA.                           497
```

Figure 3C

RV1BS nucleotide sequence

```
          10        20        30        40
AGGAGCCAGAAAGTCGTGAATGTGGCAGCTTCTCAACAGC   40
CCACTCCCGCCACGGTTGCAAGCCGTGGTCGATCCGCCGC   80
CCCTGAGCGGATGACAGGTGCACAGGCAATTGTTCGATCG  120
CTCGAGGAGCTTAACGCCGACATCGTGTTCGGTATTCCTG  160
GTGGTGCGGTGCTACCGGTGTATGACCCGCTCTATTCCTC  200
         210       220       230       240
CACAAAGGTGCGCCACGTCCTAGTGCGCCACGAGCAGGGC  240
GCAGGCCACGCAGCAACCGGCTACGCGCAGGTTACTGGAC  280
GCGTTGGCGTCTGCATTGCAACCTCTGGCCCAGGCGCAAC  320
CAACTTGGTTACCCCAATCGCTGATGCAAACTTGGACTCC  360
GTTCCCATGGTTGCCATCACCGGCCAGGTCGGAAGTAGCC  400
         410       420       430       440
TGCTGGGTACCGATGCTTTCCAGGAAGCCGATATCCGCGG  440
CATCACCATGCCAGTGACCAAGCACAACTTCATGGTCACC  480
AACCCCAACGACATTCCACAGGCATTGGCTGAGGCATTCC  520
ACCTCGCGATTACTGGTCGCCCTGGTCCTGTTCTAGTGGA  560
TATCCCCAAGGATGTTCAGAACGCTGAATTGGATTTCGTC  600
         610       620       630       640
TGGCCACCAAAGATCGACCTGCCAGGCTACCGCCCAGTTT  640
CAACACCGCATGCTCGACAGATTGAGCAGGCTGTCAAACT  680
GATCGGTGAGTCTAAGAAGCCTGTCCTTTACGTTGGCGGC  720
GGCGTTATCAAGGCTGATGCCCACGAAGAGCTTCGTGCGT  760
TCGCTGAGCACACCGGCATTCCAGTTGTCACCACATTGAT  800
```

Figure 4A

RV1B5 nucleotide sequence

```
       810       820       830       840
   |....|....|....|....|....|....|....|....|
GGCGCTGGGAACCTTCCCAGAGTCCCACGAGCTGCACATG   840
GGTATGCCAGGCATGCATGGCACTGTGTCCGCTGTTGGTG   880
CACTGCAGCGCAGCGACCTGCTGATTGCTATCGGCTCCCG   920
CTTTGATGACCGCGTCACCGGTGACGTTGACACTTTCGCA   960
CCTGATGCCAAGATCATTCACGCCGACATTGATCCTGCCG  1000
      1010      1020      1030      1040
   |....|....|....|....|....|....|....|....|
AAATCGGCAAGATCAAGCAGGTTGAGGTTCCAATCGTGGG  1040
CGATGCCCGCGAGGTTCTTGCTCGTCTGCTCGAAACCACC  1080
AAGGCAAGCAAGGCAGAGTCTGAGGACATCTCCGAGTGGG  1120
TTGACTACCTCAAGGGCCTCAAGGCACGTTTCCCACGTGG  1160
CTACGACGAGCAGCCAGGCGATCTGCTGGCACCACAGTTT  1200
      1210      1220      1230      1240
   |....|....|....|....|....|....|....|....|
GTCATTGAAACCCTGTCCAAGGAAGTTGGCCCCGACGCAA  1240
TTTACTGCGCCGGCGTTGGCCAGCACCAGATGTGGGCAGC  1280
TCAGTTCGTTGACTTCGAAAAGCCACGCACCTGGCTCAAC  1320
TCCGGTGGACTGGGCACCATGGGCTACGCAGTTCCTGCGG  1360
CTCTTGGAGCAAAGGCTGGCGCACCTGACAAGGAAGTCTG  1400
      1410      1420      1430      1440
   |....|....|....|....|....|....|....|....|
GGCTATCGACGGCGACGGCTGTTTCCAGATGACCAACCAG  1440
GAACTCACCACCGCCGCAGTTGAAGGTTTCTCCATTAAGA  1480
TCGCACTAATCAACAACGGAAACCTGGGTATGGTTCGCCA  1520
ATGGCAGACCCTATTCTATGAAGGACGGTACTCAAATACT  1560
AAACTTCGTAACCAGGGCGAGTACATGCCCGACTTTGTTA  1600
      1610      1620      1630      1640
   |....|....|....|....|....|....|....|....|
CCCTTTCTGAGGGACTTGGCTGTGTTGCCATCCGCGTCAC  1640
CAAAGCGGAGGAAGTACTGCCAGCCATCCAAAAGGCTCGA  1680
GAGATCAACGACCGCCCAGTAGTCATCGACTTCATCGTCG  1720
GTGAAGACGCACAGGTATGGCCAATGGTGTCTGCTGGATC  1760
ATCCAACTCCGATATCCAGTACGCACTCGGATTGCGCCCA  1800
```

Figure 4B

RV185 Nucleotide Sequence

```
          1810         1820         1830         1840
    |....|....|....|....|....|....|....|....|....|
TTCTTTGATGGTGATGAATCTGCAGCAGAAGATCTGCCGA  1840
CATTCACGAAGCCGTCAGCGACATTGATGCCGCCGTTGAA  1880
TCGACCGAGGCATAAGGAGAGACCCAAGATGGCTAATTCT  1920
GACGTCACCCGCCACATCCTGTCCGTACTCGTTCAGGACG  1960
TAGACGGAATCATTTCCCGCGTATCAGGTATGTTCACCCG  2000
          2010         2020         2030         2040
    |....|....|....|....|....|....|....|....|....|
ACGCGCATTCAACCTCGTGTCCCTCGTGTCTGCAAAGACC  2040
GAAACACTCGGCATCAACCGCATCACGGTTGTTGTCGACG  2080
CCGACGAGCTCAACATTGAGCAGATCACCAAGCAGCTCAA  2120
CAAGCTGATCCCCGTGCTCAAAGTCGTGCGACTTGATGAA  2160
GAGACCACTATCGCCCGCGCAATCATGCTGGTTAAGGTTT  2200
          2210         2220         2230         2240
    |....|....|....|....|....|....|....|....|....|
CTGCGGACAGCACCAACCGTCCGCAGATCGTCGACGCCGC  2240
GAACATCTTCCGCGCCCGAGTCGTCGACGTGGCTCCAGAC  2280
TCTGTGGTTATTGAATCCACAGGCACCCCAGGCAAGCTCC  2320
GCGCACTGCTTGACGTGATGGAACCATTCGGAATCCGCGA  2360
ACTGATCCAATCCGGACAGATTGCACTCAACCGCGGTCCG  2400
          2410         2420         2430         2440
    |....|....|....|....|....|....|....|....|....|
AAGACCATGGCTCCGGCCAAGATCTAA  2427
```

Figure 4C

RV1B5 Amino Acid Sequence

```
              10        20        30        40
     ....|....|....|....|....|....|....|....|
     MNVAASQQPTPATVASRGRSAAPERMTGAQAIVRSLEELN  40
     ADIVFGIPGGAVLPVYDPLYSSTKVRHVLVRHEQGAGHAA  80
     TGYAQVTGRVGVCIATSGPGATNLVTPIADANLDSVPMVA  120
     ITGQVGSSLLGTDAFQEADIRGITMPVTKHNFMVTNPNDI  160
     PQALAEAFHLAITGRPGPVLVDIPKDVQNAELDFVWPPKI  200
             210       220       230       240
     ....|....|....|....|....|....|....|....|
     DLPGYRPVSTPHARQIEQAVKLIGESKKPVLYVGGGVIKA  240
     DAHEELRAFAEHTGIPVVTTLMALGTFPESHELHMGMPGM  280
     HGTVSAVGALQRSDLLIAIGSRFDDRVTGDVDTFAPDAKI  320
     IHADIDPAEIGKIKQVEVPIVGDAREVLARLLETTKASKA  360
     ESEDISEWVDYLKGLKARFPRGYDEQPGDLLAPQFVIETL  400
             410       420       430       440
     ....|....|....|....|....|....|....|....|
     SKEVGPDAIYCAGVGQHQMWAAQFVDFEKPRTWLNSGGLG  440
     TMGYAVPAALGAKAGAPDKEVWAIDGDGCFQMTNQELTTA  480
     AVEGFSIKIALINNGNLGMVRQWQTLFYEGRYSNTKLRNQ  520
     GEYMPDFVTLSEGLGCVAIRVTKAEEVLPAIQKAREINDR  560
     PVVIDFIVGEDAQVWPMVSAGSSNSDIQYALGLRPFFDGD  600
             610       620       630       640
     ....|....|....|....|....|....|....|....|
     ESAAEDLPTFTKPSATLMPPLNRPRHKERPKMANSDVTRH  640
     ILSVLVQDVDGIISRVSGMFTRRAFNLVSLVSAKTETLGI  680
     NRITVVVDADELNIEQITKQLNKLIPVLKVVRLDEETTIA  720
     RAIMLVKVSADSTNRPQIVDAANIFRARVVDVAPDSVVIE  760
     STGTPGKLRALLDVMEPFGIRELIQSGQIALNRGPKTMAP  800
             810       820       830       840
     ....|....|....|....|....|....|....|....|
     AKI  804
```

Figure 4D

SEQUENCE LISTING

<160> NUMBER OF SEQ ID NOS: 6

<210> SEQ ID NO 1
<211> LENGTH: 1895
<212> TYPE: DNA
<213> ORGANISM: Corynebacterium sp.

<400> SEQUENCE: 1

```
ggagccagaa agtcgtgaat gtggcagctt ctcaacagcc cactcccgcc acggttgcaa      60
gccgtggtcg atccgccgcc cctgagcgga tgacaggtgc aaaggcaatt gttcgatcgc     120
tcgaggagct taacgccgac atcgtgttcg gtattcctgg tggtgcggtg ctaccggtgt     180
atgacccgct ctattcctcc acaaaggtgc gccacgtctt ggtgcgccac gagcagggcg     240
caggccacgc agcaaccggc tacgcgcagg ttactggacg cgttggcgtc tgcattgcaa     300
cctctggccc aggagcaacc aacttggtta ccccaatcgc tgatgcaaac ttggactccg     360
ttcccatggt tgccatcacc ggccaggtcg aagtggcct gctgggtacc gacgctttcc      420
aggaagccga tatccgcggc atcaccatgc agtgaccaa gcacaacttc atggtcacca     480
accctaacga cattccacag gcattggctg aggcattcca cctcgcgatt actggtcgcc     540
ctggccctgt tctggtggat attcctaagg atgtccagaa cgctgaattg gatttcgtct     600
ggccaccaaa gatcgacctg ccaggctacc gcccagtttc aacaccacat gctcgccaga     660
tcgagcaggc agtcaagctg atcggtgagg ccaagaagcc cgtccttac gttggtggtg      720
gcgtaatcaa ggctgacgca cacgaagagc ttcgtgcgtt cgctgagtac accggcatcc     780
cagttgtcac caccttgatg gctttgggta ctttcccaga gtctcacgag ctgcacatgg     840
gtatgccagg catgcatggc actgtgtccg ctgttggtgc actgcagcgc agcgacctgc     900
tgattgctat cggctcccgc tttgatgacc gcgtcaccgg tgacgttgac accttcgcgc     960
ctgacgccaa gatcattcac gccgacattg atcctgccga aatcggcaag atcaagcagg    1020
ttgaggttcc aatcgtgggc gatgcccgcg aagttcttgc tcgtctgctg gaaaccacca    1080
aggcaagcaa ggcagagacc gaggacatct ccgagtgggt tgactacctc aagggcctca    1140
aggcacgttt cccgcgtggc tacgacgagc agccaggcga tctgctggca ccacagtttg    1200
```

```
tcattgaaac cctgtccaag gaagttggcc ccgacgcaat ttactgcgcc ggcgttggcc   1260
agcaccaaat gtgggcagct cagttcgttg actttgaaaa gccacgcacc tggctcaact   1320
ccggtggact gggcaccatg gctacgcag ttcctgcggc ccttggagca aaggctggcg    1380
```
(correction)
```
ccggtggact gggcaccatg gctacgcag  ttcctgcggc ccttggagca aaggctggcg   1380
cacctgacaa ggaagtctgg gctatcgacg gcgacggctg tttccagatg accaaccagg   1440
aactcaccac cgccgcagtt gaaggtttcc ccattaagat cgcactaatc aacaacggaa   1500
acctgggcat ggttcgccaa tggcagaccc tattctatga aggacggtac tcaaatacta   1560
aacttcgtaa ccagggcgag tacatgcccg actttgttac cctttctgag ggacttggct   1620
gtgttgccat ccgcgtcacc aaagcggagg aagtactgcc agccatccaa aaggctcgag   1680
agatcaacga ccgcccagta gtcatcgact tcatcgtcgg tgaagacgca caggtatggc   1740
caatggtgtc tgctggatca tccaactccg atatccagta cgcactcgga ttgcgcccat   1800
tctttgatgg tgatgaatct gcagcagaag atcctgccga cattcacgaa gccgtcagcg   1860
acattgatgc cgccgttgaa tcgaccgagg cataa                             1895
```

<210> SEQ ID NO 2
<211> LENGTH: 626
<212> TYPE: PRT
<213> ORGANISM: Corynebacterium sp.

<400> SEQUENCE: 2

```
Met Asn Val Ala Ala Ser Gln Gln Pro Thr Pro Ala Thr Val Ala Ser
  1               5                  10                  15

Arg Gly Arg Ser Ala Ala Pro Glu Arg Met Thr Gly Ala Lys Ala Ile
             20                  25                  30

Val Arg Ser Leu Glu Glu Leu Asn Ala Asp Ile Val Phe Gly Ile Pro
         35                  40                  45

Gly Gly Ala Val Leu Pro Val Tyr Asp Pro Leu Tyr Ser Ser Thr Lys
     50                  55                  60

Val Arg His Val Leu Val Arg His Glu Gln Gly Ala Gly His Ala Ala
 65                  70                  75                  80

Thr Gly Tyr Ala Gln Val Thr Gly Arg Val Gly Val Cys Ile Ala Thr
                 85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Gln Glu Ala Asp Ile Arg Gly Ile Thr
    130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Val Gly Gly Val Ile Lys Ala
225                 230                 235                 240

Asp Ala His Glu Glu Leu Arg Ala Phe Ala Glu Tyr Thr Gly Ile Pro
```

```
                245                 250                 255
Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
            275                 280                 285

Ala Leu Gln Arg Ser Asp Leu Leu Ile Ala Ile Gly Ser Arg Phe Asp
            290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
                340                 345                 350

Glu Thr Thr Lys Ala Ser Lys Ala Glu Thr Glu Asp Ile Ser Glu Trp
            355                 360                 365

Val Asp Tyr Leu Lys Gly Leu Lys Ala Arg Phe Pro Arg Gly Tyr Asp
            370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
            450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
            530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
            595                 600                 605

Asp Ile His Glu Ala Val Ser Asp Ile Asp Ala Ala Val Glu Ser Thr
            610                 615                 620

Glu Ala
625

<210> SEQ ID NO 3
<211> LENGTH: 1505
<212> TYPE: DNA
<213> ORGANISM: Corynebacterium sp.
```

<400> SEQUENCE: 3

```
ggagccagaa agtcgtgaat gtggcagctt ctcaacagcc cactcccgcc acggttgcaa      60
gccgtggtcg atccgccgcc cctgagcgga tgacaggtgc aaaggcaatt gttcgatcgc     120
tcgaggagct taacgccgac atcgtgttcg gtattcctgg tggtgcggtg ctaccggtgt     180
atgacccgct ctattcctcc acaaaggtgc gccacgtctt ggtgcgccac gagcagggcg     240
caggccacgc agcaaccggc tacgcgcagg ttactggacg cgttggcgtc tgcattgcaa     300
cctctggccc aggagcaacc aacttggtta ccccaatcgc tgatgcaaac ttggactccg     360
ttcccatggt tgccatcacc ggccaggtcg aagtggcct gctgggtacc gacgctttcc      420
aggaagccga tatccgcggc atcaccatgc cagtgaccaa gcacaacttc atggtcacca     480
accctaacga cattccacag gcattggctg aggcattcca cctcgcgatt actggtcgcc     540
ctggccctgt tctggtggat attcctaagg atgtccagaa cgctgaattg gatttcgtct     600
ggccaccaaa gatcgacctg ccaggctacc gcccagtttc aacaccacat gctcgccaga     660
tcgagcaggc agtcaagctg atcggtgagg ccaagaagcc cgtccttac gttggtggtg      720
gcgtaatcaa ggctgacgca cacgaagagc ttcgtgcgtt cgctgagtac accggcatcc     780
cagttgtcac caccttgatg gctttgggta cttttcccaga gtctcacgag ctgcacatgg    840
gtatgccagg catgcatggc actgtgtccg ctgttggtgc actgcagcgc agcgacctgc     900
tgattgctat cggctcccgc tttgatgacc gcgtcaccgg tgacgttgac accttcgcgc     960
ctgacgccaa gatcattcac gccgacattg atcctgccga aatcggcaag atcaagcagg    1020
ttgaggttcc aatcgtgggc gatgcccgcg aagttcttgc tcgtctgctg aaaccacca     1080
aggcaagcaa ggcagagacc gaggacatct ccgagtgggt tgactacctc aagggcctca    1140
aggcacgttt cccgcgtggc tacgacgagc agccaggcga tctgctggca ccacagtttg    1200
tcattgaaac cctgtctgag ggacttggct gtgttgccat ccgcgtcacc aaagcggagg    1260
aagtactgcc agccatccaa aaggctcgag agatcaacga ccgcccagta gtcatcgact    1320
tcatcgtcgg tgaagacgca caggtatggc caatggtgtc tgctggatca tccaactccg    1380
atatccagta cgcactcgga ttgcgcccat tctttgatgg tgatgaatct gcagcagaag    1440
atcctgccga cattcacgaa gccgtcagcg acattgatgc cgccgttgaa tcgaccgagg    1500
cataa                                                                1505
```

<210> SEQ ID NO 4
<211> LENGTH: 496
<212> TYPE: PRT
<213> ORGANISM: Corynebacterium sp.

<400> SEQUENCE: 4

```
Met Asn Val Ala Ala Ser Gln Gln Pro Thr Pro Ala Thr Val Ala Ser
  1               5                  10                  15

Arg Gly Arg Ser Ala Ala Pro Glu Arg Met Thr Gly Ala Lys Ala Ile
             20                  25                  30

Val Arg Ser Leu Glu Glu Leu Asn Ala Asp Ile Val Phe Gly Ile Pro
         35                  40                  45

Gly Gly Ala Val Leu Pro Val Tyr Asp Pro Leu Tyr Ser Ser Thr Lys
     50                  55                  60

Val Arg His Val Leu Val Arg His Glu Gln Gly Ala Gly His Ala Ala
 65                  70                  75                  80

Thr Gly Tyr Ala Gln Val Thr Gly Arg Val Gly Val Cys Ile Ala Thr
```

-continued

```
                85                  90                  95
Ser Gly Pro Gly Ala Thr Asn Leu Val Thr Pro Ile Ala Asp Ala Asn
            100                 105                 110
Leu Asp Ser Val Pro Met Val Ala Ile Thr Gly Gln Val Gly Ser Gly
            115                 120                 125
Leu Leu Gly Thr Asp Ala Phe Gln Glu Ala Asp Ile Arg Gly Ile Thr
            130                 135                 140
Met Pro Val Thr Lys His Asn Phe Met Val Thr Asn Pro Asn Asp Ile
145                 150                 155                 160
Pro Gln Ala Leu Ala Glu Ala Phe His Leu Ala Ile Thr Gly Arg Pro
                165                 170                 175
Gly Pro Val Leu Val Asp Ile Pro Lys Asp Val Gln Asn Ala Glu Leu
            180                 185                 190
Asp Phe Val Trp Pro Pro Lys Ile Asp Leu Pro Gly Tyr Arg Pro Val
            195                 200                 205
Ser Thr Pro His Ala Arg Gln Ile Glu Gln Ala Val Lys Leu Ile Gly
            210                 215                 220
Glu Ala Lys Lys Pro Val Leu Tyr Val Gly Gly Val Ile Lys Ala
225                 230                 235                 240
Asp Ala His Glu Glu Leu Arg Ala Phe Ala Glu Tyr Thr Gly Ile Pro
                245                 250                 255
Val Val Thr Thr Leu Met Ala Leu Gly Thr Phe Pro Glu Ser His Glu
            260                 265                 270
Leu His Met Gly Met Pro Gly Met His Gly Thr Val Ser Ala Val Gly
            275                 280                 285
Ala Leu Gln Arg Ser Asp Leu Leu Ile Ala Ile Gly Ser Arg Phe Asp
            290                 295                 300
Asp Arg Val Thr Gly Asp Val Asp Thr Phe Ala Pro Asp Ala Lys Ile
305                 310                 315                 320
Ile His Ala Asp Ile Asp Pro Ala Glu Ile Gly Lys Ile Lys Gln Val
                325                 330                 335
Glu Val Pro Ile Val Gly Asp Ala Arg Glu Val Leu Ala Arg Leu Leu
            340                 345                 350
Glu Thr Thr Lys Ala Ser Lys Ala Glu Thr Glu Asp Ile Ser Glu Trp
            355                 360                 365
Val Asp Tyr Leu Lys Gly Leu Lys Ala Arg Phe Pro Arg Gly Tyr Asp
            370                 375                 380
Glu Gln Pro Gly Asp Leu Leu Ala Pro Gln Phe Val Ile Glu Thr Leu
385                 390                 395                 400
Ser Glu Gly Leu Gly Cys Val Ala Ile Arg Val Thr Lys Ala Glu Glu
                405                 410                 415
Val Leu Pro Ala Ile Gln Lys Ala Arg Glu Ile Asn Asp Arg Pro Val
            420                 425                 430
Val Ile Asp Phe Ile Val Gly Glu Asp Ala Gln Val Trp Pro Met Val
            435                 440                 445
Ser Ala Gly Ser Ser Asn Ser Asp Ile Gln Tyr Ala Leu Gly Leu Arg
            450                 455                 460
Pro Phe Phe Asp Gly Asp Glu Ser Ala Ala Glu Asp Pro Ala Asp Ile
465                 470                 475                 480
His Glu Ala Val Ser Asp Ile Asp Ala Ala Val Glu Ser Thr Glu Ala
                485                 490                 495
```

<210> SEQ ID NO 5

<211> LENGTH: 2427
<212> TYPE: DNA
<213> ORGANISM: Corynebacterium sp.

<400> SEQUENCE: 5

```
aggagccaga aagtcgtgaa tgtggcagct tctcaacagc ccactcccgc cacggttgca    60
agccgtggtc gatccgccgc ccctgagcgg atgacaggtg cacaggcaat tgttcgatcg   120
ctcgaggagc ttaacgccga catcgtgttc ggtattcctg gtggtgcggt gctaccggtg   180
tatgacccgc tctattcctc cacaaaggtg cgccacgtcc tagtgcgcca cgagcagggc   240
gcaggccacg cagcaaccgg ctacgcgcag gttactggac gcgttggcgt ctgcattgca   300
acctctggcc caggcgcaac caacttggtt accccaatcg ctgatgcaaa cttggactcc   360
gttcccatgg ttgccatcac cggccaggtc ggaagtagcc tgctgggtac cgatgctttc   420
caggaagccg atatccgcgg catcaccatg ccagtgacca agcacaactt catggtcacc   480
aaccccaacg acattccaca ggcattggct gaggcattcc acctcgcgat tactggtcgc   540
cctggtcctg ttctagtgga tatccccaag gatgttcaga acgctgaatt ggatttcgtc   600
tggccaccaa agatcgacct gccaggctac cgcccagttt caacaccgca tgctcgacag   660
attgagcagg ctgtcaaact gatcggtgag tctaagaagc ctgtccttta cgttggcggc   720
ggcgttatca aggctgatgc ccacgaagag cttcgtgcgt tcgctgagca caccggcatt   780
ccagttgtca ccacattgat ggcgctggga accttcccag agtcccacga gctgcacatg   840
ggtatgccag gcatgcatgg cactgtgtcc gctgttggtg cactgcagcg cagcgacctg   900
ctgattgcta tcggctcccg ctttgatgac cgcgtcaccg gtgacgttga cactttcgca   960
cctgatgcca agatcattca cgccgacatt gatcctgccg aaatcggcaa gatcaagcag  1020
gttgaggttc caatcgtggg cgatgcccgc gaggttcttg ctcgtctgct cgaaaccacc  1080
aaggcaagca aggcagagtc tgaggacatc tccgagtggg ttgactacct caagggcctc  1140
aaggcacgtt tcccacgtgg ctacgacgag cagccaggcg atctgctggc accacagttt  1200
gtcattgaaa ccctgtccaa ggaagttggc cccgacgcaa tttactgcgc cggcgttggc  1260
cagcaccaga tgtgggcagc tcagttcgtt gacttcgaaa agccacgcac ctggctcaac  1320
tccggtggac tgggcaccat gggctacgca gttcctgcgg ctcttggagc aaaggctggc  1380
gcacctgaca aggaagtctg ggctatcgac ggcgacggct gtttccagat gaccaaccag  1440
gaactcacca ccgccgcagt tgaaggtttc tccattaaga tcgcactaat caacaacgga  1500
aacctgggta tggttcgcca atggcagacc ctattctatg aaggacggta ctcaaatact  1560
aaacttcgta accagggcga gtacatgccc gactttgtta ccctttctga gggacttggc  1620
tgtgttgcca tccgcgtcac caaagcggag gaagtactgc cagccatcca aaaggctcga  1680
gagatcaacg accgcccagt agtcatcgac ttcatcgtcg gtgaagacgc acaggtatgg  1740
ccaatggtgt ctgctggatc atccaactcc gatatccagt acgcactcgg attgcgccca  1800
ttctttgatg gtgatgaatc tgcagcagaa gatctgccga cattcacgaa gccgtcagcg  1860
acattgatgc cgccgttgaa tcgaccgagg cataaggaga gacccaagat ggctaattct  1920
gacgtcaccc gccacatcct gtccgtactc gttcaggacg tagacggaat catttcccgc  1980
gtatcaggta tgttcacccg acgcgcattc aacctcgtgt ccctcgtgtc tgcaaagacc  2040
gaaacactcg gcatcaaccg catcacggtt gttgtcgacg ccgacgagct caacattgag  2100
cagatcacca agcagctcaa caagctgatc cccgtgctca agtcgtgcg acttgatgaa  2160
gagaccacta tcgcccgcgc aatcatgctg gttaaggttt ctgcggacag caccaaccgt  2220
```

```
ccgcagatcg tcgacgccgc gaacatcttc cgcgcccgag tcgtcgacgt ggctccagac    2280
tctgtggtta ttgaatccac aggcacccca ggcaagctcc gcgcactgct tgacgtgatg    2340
gaaccattcg gaatccgcga actgatccaa tccggacaga ttgcactcaa ccgcggtccg    2400
aagaccatgg ctccggccaa gatctaa                                        2427

<210> SEQ ID NO 6
<211> LENGTH: 803
<212> TYPE: PRT
<213> ORGANISM: Corynebacterium sp.

<400> SEQUENCE: 6

Met Asn Val Ala Ala Ser Gln Gln Pro Thr Pro Ala Thr Val Ala Ser
 1               5                  10                  15

Arg Gly Arg Ser Ala Ala Pro Glu Arg Met Thr Gly Ala Gln Ala Ile
             20                  25                  30

Val Arg Ser Leu Glu Glu Leu Asn Ala Asp Ile Val Phe Gly Ile Pro
         35                  40                  45

Gly Gly Ala Val Leu Pro Val Tyr Asp Pro Leu Tyr Ser Ser Thr Lys
     50                  55                  60

Val Arg His Val Leu Val Arg His Glu Gln Gly Ala Gly His Ala Ala
 65                  70                  75                  80

Thr Gly Tyr Ala Gln Val Thr Gly Arg Val Gly Val Cys Ile Ala Thr
                 85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Ser
        115                 120                 125

Leu Leu Gly Thr Asp Ala Phe Gln Glu Ala Asp Ile Arg Gly Ile Thr
    130                 135                 140

Met Pro Val Thr Lys His Asn Phe Met Val Thr Asn Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ser Lys Lys Pro Val Leu Tyr Val Gly Gly Gly Val Ile Lys Ala
225                 230                 235                 240

Asp Ala His Glu Glu Leu Arg Ala Phe Ala Glu His Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335
```

```
Glu Val Pro Ile Val Gly Asp Ala Arg Glu Val Leu Ala Arg Leu Leu
            340                 345                 350

Glu Thr Thr Lys Ala Ser Lys Ala Glu Ser Glu Asp Ile Ser Glu Trp
        355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Ser Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Leu Pro
        595                 600                 605

Thr Phe Thr Lys Pro Ser Ala Thr Leu Met Pro Pro Leu Asn Arg Pro
    610                 615                 620

Arg His Lys Glu Arg Pro Lys Met Ala Asn Ser Asp Val Thr Arg His
625                 630                 635                 640

Ile Leu Ser Val Leu Val Gln Asp Val Asp Gly Ile Ile Ser Arg Val
                645                 650                 655

Ser Gly Met Phe Thr Arg Arg Ala Phe Asn Leu Val Ser Leu Val Ser
            660                 665                 670

Ala Lys Thr Glu Thr Leu Gly Ile Asn Arg Ile Thr Val Val Val Asp
        675                 680                 685

Ala Asp Glu Leu Asn Ile Glu Gln Ile Thr Lys Gln Leu Asn Lys Leu
    690                 695                 700

Ile Pro Val Leu Lys Val Val Arg Leu Asp Glu Glu Thr Thr Ile Ala
705                 710                 715                 720

Arg Ala Ile Met Leu Val Lys Val Ser Ala Asp Ser Thr Asn Arg Pro
                725                 730                 735

Gln Ile Val Asp Ala Ala Asn Ile Phe Arg Ala Arg Val Val Asp Val
            740                 745                 750
```

```
Ala Pro Asp Ser Val Val Ile Glu Ser Thr Gly Thr Pro Gly Lys Leu
        755             760             765

Arg Ala Leu Leu Asp Val Met Glu Pro Phe Gly Ile Arg Glu Leu Ile
        770             775             780

Gln Ser Gly Gln Ile Ala Leu Asn Arg Gly Pro Lys Thr Met Ala Pro
785             790             795             800

Ala Lys Ile
```

METABOLIC ENGINEERING OF AMINO ACID PRODUCTION

CROSS-REFERENCE TO RELATED APPLICATIONS

This application is a continuation of U.S. patent application Ser. No. 11/320,139, filed Dec. 28, 2005, now U.S. Pat. No. 7,323,321 which is a continuation of U.S. patent application Ser. No. 09/630,453, filed on Aug. 2, 2000, now abandoned, which claimed priority to U.S. Provisional Patent Application No. 60/146,379, filed on Aug. 2, 1999, now abandoned. All priority applications are incorporated by reference herein.

BACKGROUND OF THE INVENTION

1. Field of the Invention

The invention relates to the areas of microbial genetics and recombinant DNA technology. More specifically, the present invention relates to the fermentative production of amino acids. The invention provides microorganisms useful for the production of amino acids, methods to increase the production of amino acids and processes for the production of amino acids.

2. Related Art

The production of amino acids through fermentation enables inexpensive production from cheap carbon sources such as molasses, acetic acid and ethanol. Following the recognition that *Corynebacteria* were useful for the industrial production of amino acids (S. Kinoshita et al., *Proceedings of the International Symposium on Enzyme Chemistry* 2: 464-468 (1957)), commercial production of amino acids by fermentative processes was made more possible with the isolation of mutant strains. Microorganisms employed in microbial processes for amino acid production may be divided into 4 classes: wild-type strain, auxotrophic mutant, regulatory mutant and auxotrophic regulatory mutant (K. Nakayama et al, in NUTRITIONAL IMPROVEMENT OF FOOD AND FEED PROTEINS, M. Friedman, ed., (1978), pp. 649-661). The stereospecificity of the amino acids produced by fermentation makes the process advantageous compared with synthetic processes; amino acids produced by microbial process are generally the L-form.

L-lysine is one example of an amino acid produced by industrial fermentation. Commercial production of this essential amino acid is principally done utilizing the gram positive *Corynebacterium glutamicum*, *Brevibacterium flavum* and *Brevibacterium lactofermentum* (Kleemann, A., et. al., Amino Acids, in ULLMAN'S ENCYCLOPEDIA of INDUSTRIAL CHEMISTRY, vol. A2, pp. 57-97, Weinham: VCH-Verlagsgesellschaft (1985)); cumulatively, these three organisms presently account for the approximately 250,000 tons of L-lysine produced annually.

Given the economic importance of L-lysine production by fermentive processes, it would be beneficial to increase the total amount produced while simultaneously decreasing production costs. To that end, the biochemical pathway for L-lysine synthesis has been intensively investigated in *Corynebacterium* (recently reviewed by Sahm et al., *Ann. N.Y. Acad. Sci.* 782: 25-39 (1996)). Entry into the lysine pathway begins with L-aspartate (see FIG. 1), which itself is produced by transamination of oxaloacetate. A special feature of *C. glutamicum* is its ability to convert the lysine intermediate piperideine 2,6-dicarboxylate to diaminopimelate by two different routes, i.e. by reactions involving succinylated intermediates or by the single reaction of diaminopimelate dehydrogenase. Overall, carbon flux into the pathway is regulated at two points: first, through feedback inhibition of aspartate kinase by the levels of both L-threonine and L-lysine; and second through the control of the level of dehydrodipicolinate synthase. Therefore, increased production of L-lysine may be obtained in *Corynebacteria* by deregulating and increasing the activity of these two enzymes.

In addition to the biochemical pathway leading to L-lysine synthesis, recent evidence indicates that consideration of lysine transport out of cells into the media is another condition to be considered in the development of lysine overproducing strains of *C. glutamicum*. Studies by Krämer and colleagues indicate that passive transport out of the cell, as the result of a leaky membrane, is not the sole explanation for lysine efflux; their data suggest a specific carder with the following properties: (1) the transporter possesses a rather high Km value for lysine (20 mM); (2) the transporter is an $OH^-$ symport system (uptake systems are $H+$ antiport systems); and (3) the transporter is positively charged, and membrane potential stimulates secretion (S. Bröer and R. Krämer, *Eur. J. Biochem.* 202: 137-143 (1991).

Several fermentation processes utilizing various strains isolated for auxotrophic or resistance properties are known in the art for the production of L-lysine: U.S. Pat. No. 2,979,439 discloses mutants requiring homoserine (or methionine and threonine); U.S. Pat. No. 3,700,557 discloses mutants having a nutritional requirement for threonine, methionine, arginine, histidine, leucine, isoleucine, phenylalanine, cystine, or cysteine; U.S. Pat. No. 3,707,441 discloses a mutant having a resistance to a lysine analog; U.S. Pat. No. 3,687,810 discloses a mutant having both an ability to produce L-lysine and a resistance to bacitracin, penicillin G or polymyxin; U.S. Pat. No. 3,708,395 discloses mutants having a nutritional requirement for homoserine, threonine, threonine and methionine, leucine, isoleucine or mixtures thereof and a resistance to lysine, threonine, isoteucine or analogs thereof; U.S. Pat. No. 3,825,472 discloses a mutant having a resistance to a lysine analog; U.S. Pat. No. 4,169,763 discloses mutant strains of *Corynebacterium* that produce L-lysine and are resistant to at least one of aspartic analogs and sulfa drugs; U.S. Pat. No. 5,846,790 discloses a mutant strain able to produce L-glutamic acid and L-lysine in the absence of any biotin action-suppressing agent; and U.S. Pat. No. 5,650,304 discloses a strain belonging to the genus *Corynebacterium* or *Brevibacterium* for the production of L-lysine that is resistant to 4-N-(D-alanyl)-2,4-diamino-2,4-dideoxy-L-arabinose 2,4-dideoxy-L-arabinose or a derivative thereof.

More recent developments in the area of L-lysine fermentive production in *Corynebacteria* involve the use of molecular biology techniques to augment lysine production. The following examples are provided as being exemplary of the art: U.S. Pat. Nos. 4,560,654 and 5,236,831 disclose an L-lysine producing mutant strain obtained by transforming a host *Corynebacterium* or *Brevibacterium* microorganism which is sensitive to S-(2-aminoethyl)-cysteine with a recombinant DNA molecule wherein a DNA fragment conferring both resistance to S-(2-aminoethyl)-cysteine and lysine producing ability is inserted into a vector DNA; U.S. Pat. No. 5,766,925 discloses a mutant strain produced by integrating a gene coding for aspartokinase, originating from coryneform bacteria, with desensitized feedback inhibition by L-lysine and L-threonine, into chromosomal DNA of a *Coryneform* bacterium harboring leaky type homoserine dehydrogenase or a *Coryneform* bacterium deficient in homoserine dehydrogenase gene.

In addition to L-lysine, *Corynebacterium* and related organisms are useful for the production of other amino acids, for example the branched chain amino acids L-leucine, L-isoleucine and L-valine. The biochemical pathways leading to branched chain amino acid biosynthesis are also well studied. Carbon flux into the aspartate pathway may be funneled onto the production of L-lysine or L-threonine, which may be utilized for the production of L-isoleucine (FIG. 1B). L-isoleucine is produced from L-threonine in five reactions; the enzymes catalyzing these reactions include: (1) threonine dehydratase; (2) acetohydroxy acid synthase; (3) isomeroreductase; (4) dihydroxy acid dehydratase; and (5) transaminase B. Threonine dehydratase is the only enzyme in this pathway unique to isoleucine synthesis; the other four enzymes are also utilized in the production of the other branched chain amino acids, valine and leucine. Carbon flux from threonine to isoleucine is controlled by threonine dehydratase and acetohydroxy acid synthase (AHAS). With the cloning of genes encoding the enzymes of the isoleucine pathway (ilvA, ilvB, ilvC, ilvD and ilvE) in *Corynebacterium* (C. Cordes et al., *Gene* 112:113-116 (1992); B. Möckel et al., *J. Bacteriology* 174: 8065-8072 (1992); and C. Keilhauer et al., *J. Bacteriology* 175: 5595-5603 (1993)), recombinant DNA techniques may be applied to generate novel strains.

Improvements in the production of the amino acids L-isoleucine, L-leucine and L-valine by increasing the activity of enzymes in the branched chain amino acid biosynthetic pathway have been described. Additionally, improvements in the production of branched chain amino acids by improving the acetohydroxy acid synthase (AHAS) activity encoded by the ilvBN operon have been described. (see generally H. Sahm et al., *Ann. N.Y. Acad. Sci.* 782:25-39 (1996)).

Exemplary processes for the production of branched chain amino acids include the following: U.S. Pat. No. 5,188,948 discloses a fermentation process for producing L-valine utilizing a microorganism that is resistant to a polyketide; U.S. Pat. No. 5,521,074 discloses a process for producing L-valine utilizing a microorganism which belongs to the genus *Corynebacterium* or *Brevibacterium*, which exhibits a) an ability to produce L-valine, b) resistance to L-valine in a medium containing acetic acid as a sole carbon source, and c) sensitivity to a pyruvic acid analog in a medium containing glucose as a sole carbon source; U.S. Pat. No. 4,601,983 discloses a genetic sequence coding for the production of a protein having the activity of homoserine dehydrogenase capable of replication in coryneform bacteria and used to produce L-threonine and L-isoleucine; U.S. Pat. No. 4,442,208 discloses a fermentation process for the production of L-isoleucine utilizing a *Brevibacterium* or *Corynebacterium* strain obtained by recombinant DNA techniques that is resistant to α-amino-β-hydroxy valeric acid; U.S. Pat. No. 4,656,135 discloses a process for producing L-isoleucine, which comprises culturing a microorganism belonging to the genus *Brevibacterium* or the genus *Corynebacterium* which has a methyllysine resistance or α-ketomalonic acid resistance and which is capable of producing L-isoleucine in a liquid medium, and obtaining the accumulated L-isoleucine from said medium; U.S. Pat. No. 5,118,619 discloses a method for the fermentative production of L-isoleucine from D,L-α-hydroxybutyrate by means of mutants that utilize D-lactate; U.S. Pat. No. 5,763,231 discloses a process for producing L-leucine, which includes incubating a strain of the genus *Corynebacterium, Escherichia, Brevibacterium*, or *Microbacterium* in a culture medium and reacting the resulting cells with saccharides and acetic acid or its salt to form and accumulate L-leucine in the reaction solution; and U.S. Pat. No. 3,970,519 discloses strains that resist feedback inhibition by leucine or its analogs and require at least one of isoleucine, threonine or methionine as a growth nutriment to produce L-leucine.

Improvements in the production of amino acids by decreasing the production of valine have not been described.

Improvements in the production of amino acids by decreasing AHAS activity have not been described.

SUMMARY OF THE INVENTION

It is an object of the present invention to provide microorganisms that are capable of converting glucose to amino acids other than L-isoleucine, L-leucine and L-valine with greater efficiency than the parent strain. The efficiency of conversion may be quantified by the formula:

[(g amino acid produced/g dextrose consumed)*100]=% Yield and expressed as yield from dextrose.

In one embodiment, the invention provides microorganisms that are made auxotrophic for the synthesis of one or more branched chain amino acids by mutagenesis and selected for their ability to produce higher percent fields of the desired amino acid than the parental strain.

In a more specific embodiment of the invention provides microorganisms obtained by subjecting a parental strain to random chemical mutagenesis, isolating a mutagenized variant that is auxotrophic for branched chain amino acid synthesis and selecting variants that are capable of converting glucose to amino acids other than L-isoleucine, L-leucine and L-valine with greater efficiency than the parent strain. Another specific embodiment of the invention provides microorganisms obtained by utilizing rDNA methodologies to introduce a change (i.e., a mutation) in the nucleic acid sequence of the ilvBN operon, isolating a mutagenized variant that is auxotrophic or bradytrophic for branched chain amino acid synthesis and selecting variants that are capable of converting glucose to amino acids other than L-isoleucine, L-leucine and L-valine with greater efficiency than the parent strain.

In a preferred embodiment, the microorganisms of the invention produce L-lysine. Another preferred embodiment of the invention is drawn to *Corynebacterium* microorganisms, or *Brevibacterium* microorganisms, and particularly preferred microorganisms are *Corynebacterium* or *Brevibacterium* microorganisms that produce L-lysine. In a most preferred embodiment, the microorganisms have the identifying characteristics of NRRL No. B-30149 (also known as LC10) or NRRL No. B-30150 (also known as BF100-1030), strains deposited on Jun. 29, 1999 with the Agricultural Research Service Culture Collection (NRRL), 1815 North University Street, Peoria, Ill. 61604 USA.

Another object of the invention provides methods to increase the production of an amino acid by mutagenizing a parental strain, selecting cells auxotrophic for the synthesis of one or more branched chain amino acids and selecting branched chain amino acid auxotrophs that produce a higher percent yield from dextrose of the desired amino acid than the parental strain.

In a preferred embodiment, the method is drawn to increasing the yield from dextrose of the amino acid L-lysine obtained by culturing *Corynebacterium* which, through random chemical mutagenesis or recombinant DNA (rDNA) technology, is made to be auxotrophic or bradytrophic for one or more of the branched chain amino acids leucine, isoleucine and valine.

In one specific embodiment, branched chain amino acid auxotrophy is the result of chemical mutagenesis of *Corynebacterium*. In an alternative specific embodiment, branched chain amino acid auxotrophy is the result of mutagenesis of the ilvBN operon by rDNA techniques.

Another object of the invention is to provide processes for the production of an amino acid from microorganisms that are capable of converting glucose to amino acids other than L-isoleucine, L-leucine and L-valine with greater efficiency than the parent strain.

In one embodiment, the invention provides a process for producing an amino acid comprising culturing in a medium a microorganism obtained by mutagenizing a parent strain to be auxotrophic or bradytrophic for branched chain amino acid synthesis and selecting variants that are capable of converting glucose to amino acids other than L-isoleucine, L-leucine and L-valine with greater efficiency than the parent strain.

In a preferred embodiment for the process, the microorganism utilized in fermentation is obtained by subjecting the parent strain to random chemical mutaganesis, isolating a mutagenized variant that is auxotrophic for branched chain amino acid synthesis and selecting variants that are capable of convening glucose to amino acids other than L-isoleucine, L-leucine and L-valine with greater efficiency than the parent strain. In another preferred embodiment for the process, the microorganism utilized in fermentation is obtained by altering (i.e., introducing a mutation) the nucleotide sequence of the ilvBN operon by rDNA methodology, isolating a mutagenized variant that is auxotrophic or bradytrophic for branched chain amino acid synthesis and selecting variants that are capable of converting glucose to amino acids other than L-isoleucine, L-leucine and L-valine with greater efficiency than the parent strain.

It is to be understood that the foregoing general description and the following detailed description are exemplary and explanatory only and are intended to provide further explanation of the invention as claimed.

BRIEF DESCRIPTION OF THE FIGURES

FIG. 2. A-B) Presentation of the nucleotide sequence of the ilvBN operon of *Corynebacterium* (SEQ ID NO:1); C) Presentation of the amino acid sequence of the ilvBN operon of *Corynebacterium* (SEQ ID NO:2).

FIG. 3. A-B) Presentation of the nucleotide sequence for the ilvBN deletion mutant in the plasmid pAL203Δ (SEQ ID NO:3); C) Presentation of the amino acid sequence for the ilvBN deletion mutant in the plasmid pAL203Δ (SEQ ID NO:4).

FIG. 4. A-C) Presentation of the nucleotide sequence of the pRV1B5 allele (SEQ ID NO:5); D) Presentation of the amino acid sequence of the pRV1B5 allele (SEQ ID NO:6).

DETAILED DESCRIPTION OF THE PREFERRED EMBODIMENTS

1. Definitions

Figure 1A:
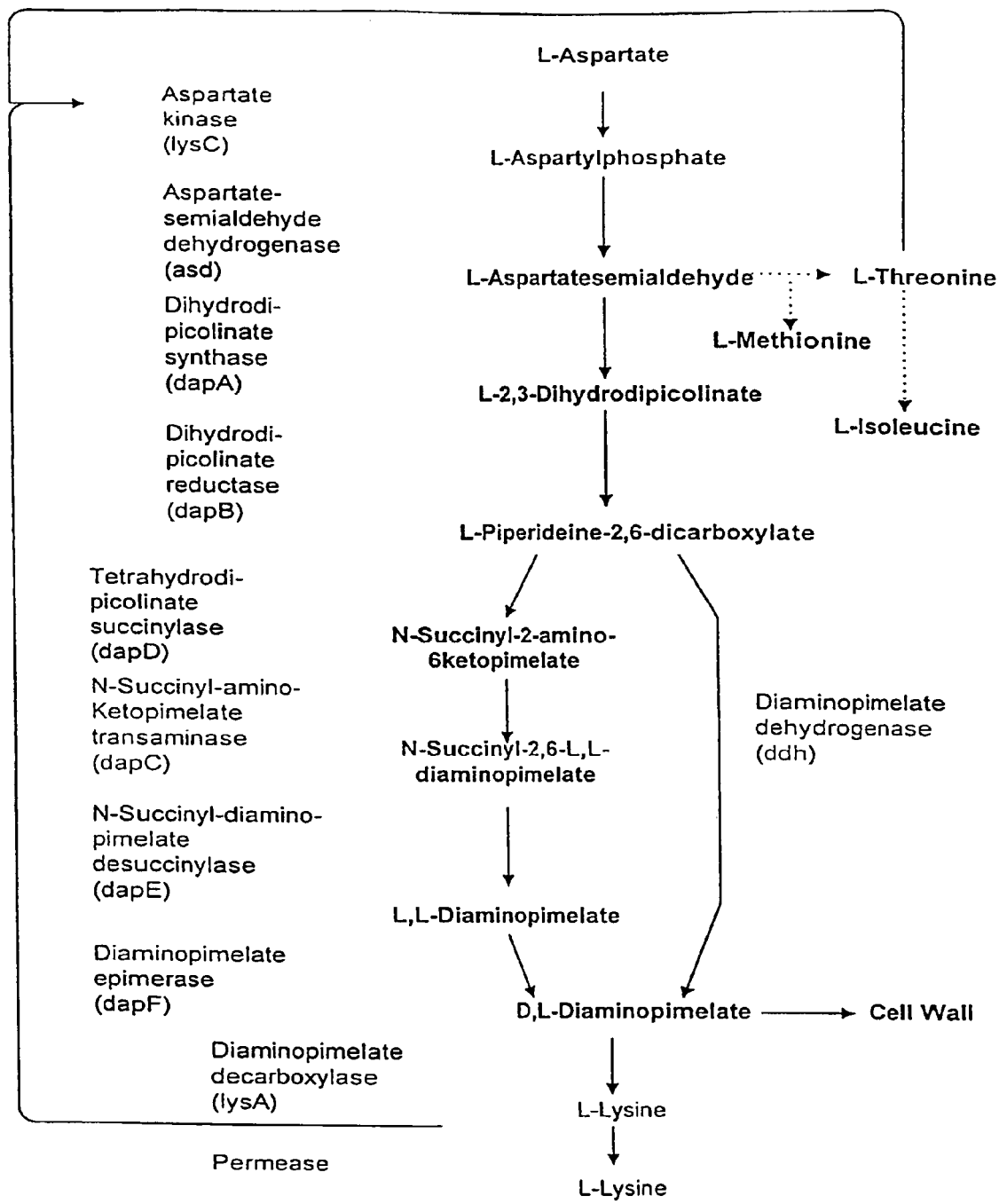
FIG. 1. (A) A schematic presentation of the biochemical pathway leading to L-lysine production in *Corynebacterium*; (B) A schematic presentation of the biochemical pathway leading to L-isoleucine production in *Corynebacterium*.
Figure 1B:
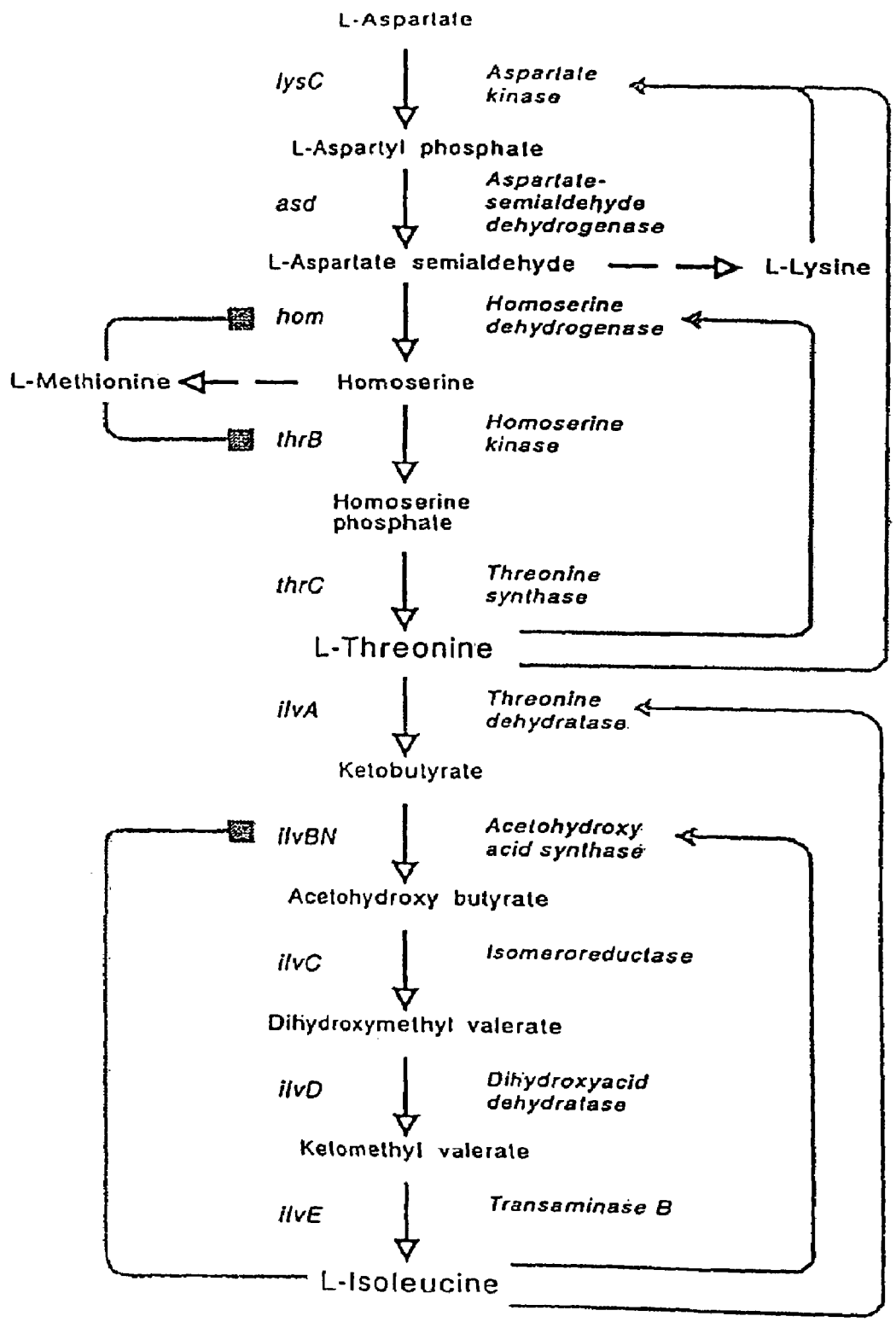

In order to provide a clear and consistent understanding of the specification and claims, including the scope to be given such terms, the following definitions are provided.

Auxotroph: As used herein, the term auxotroph refers to a strain of microorganism requiring for growth an external source of a specific metabolite that cannot be synthesized because of an acquired genetic defect.

Amino Acid Supplement: As used herein, the term "Amino Acid Supplement" refers to an amino acid required for growth and added to minimal media to support auxotroph growth.

Bradytroph: As used herein, the term bradytroph refers to a strain of microorganism that exhibits retarded growth in the absence of an external source of a specific metabolite. A bradytroph can synthesize the metabolite, but because of an acquired genetic defect, the rate of synthesis is less than the parent strain's rate of synthesis of the same metabolite.

Branched Amino Acid: As used herein, the term refers to those amino acids in which the R group possesses a branched carbon structure, such as leucine, isoleucine and valine.

Carbon Flux: As used herein, the term refers to the movement of carbon between amphibolic, catabolic and/or anabolic biochemical pathways of an organism.

Chromosomal Integration: As used herein, the term refers to the insertion of art exogeneous DNA fragment into the chromosome of a host organism; more particularly, the term is used to refer to homologous recombination between an exogenous DNA fragment and the appropriate region of the host cell chromosome.

High Yield Derivative: As used herein, the term refers to strain of microorganism that produces a higher yield from dextrose of a specific amino acid when compared with the parental strain from which it is derived.

Mutation: As used herein, the term refers to a single base pair change, insertion or deletion in the nucleotide sequence of interest.

Operon: As used herein, the term refers to a unit of bacterial gene expression and regulation, including the structural genes and regulatory elements, in DNA. Examples of regulatory elements that are encompassed within the operon include, but are not limited to, promoters and operators.

Parental Strain: As used herein, the term refers to a strain of microorganism subjected to some form of mutagenesis to yield the microorganism of the invention.

Percent Yield From Dextrose: As used herein, the term refers to the yield of amino acid from dextrose defined by the formula [(g amino acid produced/g dextrose consumed)*100] =% Yield.

Phenotype: As used herein, the term refers to observable physical characteristics dependent upon the genetic constitution of a microorganism.

Relative Growth: As used herein, the term refers to a measurement providing an assessment of growth by directly comparing growth of a parental strain with that of a progeny strain over a defined time period and with a defined medium.

Mutagenesis: As used herein, the term refers to a process whereby a mutation is generated in DNA. With "random" mutatgenesis, the exact site of mutation is not predictable, occurring anywhere in the genome of the microorganism, and the mutation is brought about as a result of physical damage caused by agents such as radiation or chemical treatment, rDNA mutagenesis is directed to a cloned DNA of interest, and it may be random or site-directed.

2. Microorganisms of the Invention Based on Decreased Carbon Flow to Branched Chain Amino Acid Synthesis and Increased Production of NonBranched Amino Acids The invention provides generally for the creation of microorganisms that are auxotrophic for the branched chain amino acid synthesis in order to direct carbon flux to non-branched chain amino acid synthesis. More specifically, by selecting for a specific auxotrophic phenotype requiring one or more of the branched chain amino acids leucine, isoleucine or valine (e.g., isoleucine and valine) or designing mutations in the ilvBN operon that decrease the flow of carbon to isoleucine, leucine and valine synthesis, carbon flux in the system may then become available for other metabolic pathways (e.g., L-lysine synthesis).

In one specific embodiment, the invention provides a microorganism C that produces amino acid X, wherein said microorganism C is obtained by the following method:
(a) selecting a parental microorganism A that produces said amino acid from dextrose in percent yield Y;
(b) mutagenizing said parental microorganism A to produce microorganism B by a method selected from the group consisting of:
    (i) random chemical mutagenesis; and
    (ii) rDNA mutagenesis of the ilvBN operon;
(c) selecting from step (b) at least one mutagenized microorganism B that is auxotrophic or bradytrophic for one or more of the branched chain amino acids leucine, isoleucine and valine; and
(d) selecting from step (c) at least one microorganism C which produces said amino acid X from dextrose in percent yield Z, wherein said percent yield Z is greater than said percent yield Y.

The percent yield from dextrose is preferably calculated using the formula [(g amino acid/L/(g dextrose consumed/L)] *100.

Parental microorganisms may be selected from any microorganism known in the art that can produce amino acid X. Particularly favored parental microorganisms *Corynebacterium* and *Brevibacterium*.

The strains of the invention may be prepared by any of the methods and techniques known and available to those skilled in the art. Illustrative examples of suitable methods for constructing the inventive bacterial strains include but are not limited to the following: mutagenesis using suitable agents such as N-methyl-N'-nitro-N-nitrosoguanidine (NTG); gene integration techniques, mediated by transforming linear DNA fragments and homologous recombination; and transduction mediated by a bacteriophage. These methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); Methods in Plant Molecular Biology and Biotechnology, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989).

A. Construction of Branched Chain Amino Acid Auxotrophs by Random Mutagenesis

One specific preferred embodiment of the invention provides that modification of an enzymatic step common to L-isoleucine, L-leucine and L-valine biosynthesis can increase the percent yield of L-lysine from dextrose.

In a most preferred embodiment, the invention provides for the production of microorganisms that are auxotrophic for branched chain amino acid synthesis by means of random mutagenesis of a parental strain followed by selection of the specific phenotype. The parental strain chosen for mutagenesis may be any strain known to produce the amino acid of interest. Preferred organisms include *Corynebacterium* strains and *Brevibacterium* strains, and most preferred organisms include *Corynebacterium* strains and *Brevibacterium* strains that produce L-lysine.

The parental strain may be mutagenized using any random mutagenesis technique known in the art, including, but not limited to, radiation and chemical procedures. Particularly preferred is random chemical mutagenesis, and most preferable is the alkylating agent method described by J. H. Miller (J. H. Miller, *Experiments in Molecular Genetics*, Cold Spring Harbor Laboratory (1972).

By way of example, chemical mutagenesis was conducted as follows. A culture of lysine-producing *Corynebacterium* strain was grown in rich medium at 30° C. up to an optical density of 6.0. Cells were washed with minimal medium and resuspended in minimal medium containing 100 micrograms per mL of NTG. Cells were exposed to the mutagen for 30 minutes at 30° C. Cells were washed with minimal medium and plated onto rich medium. Colonies from rich medium were replica-plated to rich and minimal medium. Colonies that grew on rich medium but did not grow on minimal medium were classified as auxotrophs. Auxotroph mutants were replica-plated onto minimal medium and minimal medium containing 10 mM L-isoleucine and 10 mM L-valine. Colonies that were rescued by the isoleucine and valine were classified as valine auxotrophs. Strain B4B is a valine auxotroph generated by chemical mutagenesis.

B. Construction of Branched Chain Amino Acid Auxotrophs by Mutagenesis Through rDNA Methodology Another specific preferred embodiment of the invention utilizes recombinant DNA technology to effect in vitro and in vivo mutagenesis of cloned DNA sequences that encode proteins important for the biosynthesis of branched chain amino acids. The mutated DNA may then be used to modify the parented strain to produce mutant strains that are auxotrophic for branched chain amino acid synthesis and that produce a higher yield from dextrose of non-branched chain amino acids than the parental strain.

In one specific preferred embodiment, the cloned DNA of interest may be mutated through recombinant DNA technology by any means known in the that art. As one skilled in the art would know, the mutations in the cloned DNA may constitute single nucleotide changes (point mutations), multiple nucleotide changes, nucleotide deletions or insertions. General methods for recombinant DNA technology are known to those skilled in the art and may be found in a number of common laboratory manuals that describe fundamental techniques, such as nucleic acid purification, restriction enzyme digestion, ligation, gene cloning, gene sequencing, polymerase chain amplification (PCR) of gene sequences, and the like. (see e.g., Sambrook et al., *Molecular Cloning: A Laboratory Manual*, Second Edition, Cold Spring Harbor Laboratory, Cold Spring Harbor, N.Y. (1989); Current Protocols in Molecular Biology. Ausubel et al. eds., John Wiley & Sons, New York, (1994); *PCR Protocols*, Innis et al., eds., Academic Press, Inc., New York, pp. 407-415 (1990)).

In addition, references that specifically teach in vitro mutatgenesis of cloned DNA are known to those skilled in the art. For example, strategies such as site-directed mutatgenesis, oligonucleotide-directed mutatgenesis, linker scanning mutatgenesis, random chemical mutatgenesis in vitro, cassette mutatgenesis, PCR mutatgenesis and others are detailed in *Directed Mutagenesis: A Practical Approach*, M. J. McPherson, ed., Oxford University Press, New York, (1991).

In another specific preferred embodiment, the cloned DNA of interest may be mutated in vivo in a host cell. This type of "in vivo mutagenesis" includes processes of generating random mutations in any cloned DNA of interest by the propagation of the DNA in a strain of *E. coli* that carries mutations in one or more of the DNA repair pathways. These "mutator" strains have a higher random mutation rate than that of a wild-type parent. Propagating the DNA in one of these strains will generate random mutations within the DNA. Systems designed to accomplish this are known to those skilled in the art and are available commercially. For example, Stratagene, Inc. provides a system utilizing the XL1 Red Strain of *E. coli* which has had its DNA repair genes (MutH, MutL and MutS) deleted such that many different mutations occur in a short time. Up to 10,000 mutations may take place within a 30 hour time span such that an entire mutated DNA library may be prepared from mutated DNA by procedures known in the art.

The cloned DNA selected for mutation may be any sequence known in the art to be important for branched chain amino acid synthesis, including but not limited to, sequences encoding one or more enzymes important for synthesis or one or more protein products important for transport and excretion. Most preferred is the cloned sequence for the ilvBN operon of *Corynebacterium* or *Brevibacterium*. *Corynebacterium* genes involved in branched chain amino acid synthesis have been cloned; for example, gene sequences are available for the isoleucine pathway (ilvA, itvB, ilvC, ilvD and ilvE) (C. Cordes et al., *Gene* 112: 113-116 (1992); B. Möckel et al., *J. Bacteriology* 174: 8065-8072 (1992); and C. Keilhauer et al., *J. Bacteriology* 175: 5595-5603 (1993)).

L-isoleucine is produced from L-threonine in five reactions; the enzymes catalyzing these reactions include: (1) threonine dehydratase (ilvA); (2) acetohydroxy acid synthase (ilvBN); (3) isomeroreductase (ilvC); (4) dihydroxy acid dehydratase (ilvD); and (5) transaminase B (ilvE). Threonine dehydratase is the only enzyme in this pathway unique to isoleucine synthesis; the other four enzymes are also utilized in the production of the other branched chain amino acids, valine and leucine. The enzymatic pathway involved in isoleucine biosynthesis in *Corynebacterium* strains is presented in FIG. 2.

Acetohydroxy acid synthase (AHAS) and isomeroreductase (IR) catalyze subsequent reactions in the flux of metabolites towards isoleucine, valine, leucine, and pantothenate. As in other bacteria, the AHAS of *Corynebacterium* strains is encoded by two genes, ilvB and ilvN. Gene disruption verified that these genes encode the single AHAS activity in *C. glutamicum* (Keilhauer, C., et al., *J. Bacteriology* 175:5595-5603 (1973)). Three transcripts of 3.9, 2.3, and 1.1 kb were identified in vivo by Northern Blot analysis, which correspond to ilvBNC, ilvNC, and ilvC messages, respectively. The ilvC transcript (encoding IR) is the most abundant transcript from the ilv operon of *C. glutamicum*. Additional analysis indicates that three promoters are active in this operon; the steady-state levels of the ilvBNC and ilvNC messages contribute significantly to the total activity of the single AHAS.

In a most preferred invention embodiment, a mutation may be generated by way of restriction enzyme digestion to create a deletion in the cloned ilvBN operon DNA sequence. The mutated ilvBN sequence may then be substituted for the wild type sequence by homologous recombination and screened for branched chain amino acid auxotrophy.

Another embodiment of the invention is drawn to a microorganism *Corynebacterium* having the following that is auxotrophic for the one or more of the branched chain amino acids isoleucine, leucine and valine and produces a percent yield from dextrose of the an amino acid of interest that is greater than the parental strain percent yield. In a particularly favored embodiment, the amino acid produced is L-lysine.

Other highly preferred embodiments of the invention are drawn to microorganisms having substantially all of the characteristics of NRRL Deposit No. B-30149, which was deposited on Jun. 29, 1999, with the Agricultural Research Culture Collection (1815 N. University Street, Peoria, Ill. 61604, USA) or NRRL Deposit No. B-30150, which was deposited on Jun. 29, 1999, with the Agricultural Research Culture Collection (1815 N. University Street, Peoria, Ill. 61604, USA). NRRL Deposit No. B-30149 is of the microorganism *Corynebacterium glutamicum* LC10, and NRRL Deposit No. B-30150 is of the microorganism *Corynebacterium glutamicum* BF100-1030.

3. Methods of Increasing the Production of an Amino Acid

A further object of the invention provides methods to increase the production of an amino acid. The invention provides generally for a method to increase the production of an amino acid X, comprising:
(a) selecting a parental microorganism A that produces said amino acid from dextrose in percent yield Y;
(b) mutagenizing said parental microorganism A to produce microorganism B by a method selected from the group consisting of:
  (i) random chemical mutagenesis; and
  (ii) rDNA mutagenesis of the ilvBN operon;
(c) selecting from step (b) at least one mutagenized microorganism B that is auxotrophic for one or more of the branched chain amino acids leucine, isoleucine and valine; and
(d) selecting from step (c) at least one microorganism C which produces said amino acid X from dextrose in percent yield Z, wherein said percent yield Z is greater than said percent yield Y.

In one particular preferred embodiment, any strain known in the art may be selected as a parental strain that produces the amino acid of interest at a determined percent yield from dextrose. The percent yield from dextrose may be easily calculated using the following formula: [(g amino acid/L/(g dextrose consumed/L)]*100.

After selecting the organism and determining the percent yield from dextrose of the amino acid, the microorganism is preferably subjected to mutagenesis either by random mutagenesis techniques directed at the entire genome of the organism or by rDNA techniques directed towards cloned DNA of interest. Regardless of the particular method of mutagenesis employed, mutated organisms are screened and selected on the basis of auxotrophy for branched chain amino acid synthesis. Auxotrophs selected may then be screened to determine which strains produce a higher percent yield of the desired amino acid from dextrose than the parental strain.

Various embodiments of the invention include methods to increase the production of an amino acid of interest from the organisms *Corynebacterium*, *Brevibacterium*, and *E. coli*. Additionally, depending upon the particular embodiment, the invention provides methods to increase the production of non-branched amino acids, such as glycine; alanine; methionine; phenylalanine; tryptophan; proline; serine; threonine; cysteine; tyrosine; asparagine; glutamine; aspartic acid; glutamic acid; lysine; arginine; and histidine.

In a favored embodiment, the invention provides methods to increase non-branched chain amino acid production by creating auxotrophs for branched chain amino acid synthesis and diverting carbon flux from the synthesis of leucine, isoleucine and valine. A particularly favored embodiment is drawn to a method of increasing the production of an amino acid by selecting from a mutagenized parental strain a strain that is auxotrophic for valine and isoleucine synthesis.

The invention further provides various preferred embodiments for methods to increase the production of an amino acid wherein the parental strain may be mutagenized either by random mutagenesis techniques (e.g., radiation or chemical mutagenesis) or mutagenesis of the ilvBN operon by rDNA techniques. In one particular preferred embodiment, the parental strain may be mutagenized by random chemical mutagenesis. In another particular preferred embodiment, the parental strain is mutagenized by rDNA techniques directed at the cloned ilvBN operon nucleotide sequence.

4. Processes for the Production of an Amino Acid

A further object of the invention provides processes for the production of an amino acid. The invention provides generally for a process for producing an amino acid X comprising:
(a) culturing a microorganism C in a medium, wherein said microorganism C is obtained by the following method:
  (i) selecting a parental microorganism A that produces said amino acid from dextrose in percent yield Y;
  (ii) mutagenizing said parental microorganism A to produce microorganism B by a method selected from the group consisting of:
    (a) random chemical mutagenesis; and
    (b) rDNA mutagenesis of the ilvBN operon;
  (iii) selecting from step (b) at leat one mutagenized microorganism B that is auxotrophic for one or more of the branched chain amino acids leucine, isoleucine and valine; and
  (iv) selecting from step (c) at least one microorganism C which produces said amino acid X from dextrose in percent yield Z, wherein said percent yield Z is greater than said percent yield Y; and
(b) recovering said amino acid X that is produced from said microorganism C.

Preferred embodiments of the invention are drawn to processes in which the cultured microorganism is selected from the group that includes *Corynebacterium, Brevibacterium*, and *E. coli*. Particularly preferred are process drawn to the organisms of the genus *Corynebacterium*. Microorganisms selected for the processes of the invention are those that produce an amino acid of interest, particularly non-branched chain amino acids. More particularly preferred microorganisms are microorganisms that produce glycine; alanine; methionine; phenylalanine; tryptophan; proline; serine; threonine; cysteine; tyrosine; asparagine; glutamine; aspartic acid; glutamic acid; lysine; arginine; and histidine. The level of production of the amino acid of choice may conveniently determined by the following formula to calculate the percent yield from dextrose: [(g amino acid/L/(g dextrose consumed/L)]*100.

Microorganisms used in the processes of the invention are preferably obtained by mutagenesis of the chosen parental strain. Preferred embodiments of the invention include processes in which the chosen parental strains are subjected either to random mutagenesis directed at the entire genome or to rDNA mutagenesis of cloned DNA of interest.

Particularly preferred embodiments of the invention wherein the parental strain is subjected to random mutagenesis include but are not limited to, mutagenesis by radiation treatment or chemical treatment. A more particularly preferred embodiment is drawn to random chemical mutagenesis of the parental strain.

Another particularly preferred embodiment of the invention provides for rDNA mutagenesis of the parental strain. A more particularly preferred embodiment is drawn to rDNA mutagenesis of the ilvBN operon in vitro or in vivo. Mutated forms of the ilvBN operon, or fragments thereof, may then be substituted for wild-type ilvBN operon sequence through homologous recombination techniques that are well known to those skilled in the art (see Example 6).

However the selected parental strains or cloned DNA sequences are mutagenized, the resultant progeny are screened and selected for auxotrophy for branched chain amino acid synthesis (i.e., leucine, isoleucine or valine). The selection of such mutants is well with in the skill of those in the art. A particularly preferred embodiment is drawn to strains that are auxotrophic for valine and isoleucine biosynthesis.

Ultimately, selection of the microorganisms of the processes of the invention is dependent upon production of the amino acid of choice. Utilizing the formula [(g amino acid] L/(g dextrose consumed/L)]*100 to determine the percent yield from dextrose, the desired microorganisms are selected on the basis of having a higher percent yield from dextrose of the amino acid of choice than the parental strain.

Other embodiments of the invention are drawn to processes that vary by way of the specific method of culturing the microorganisms of the invention. Thus, a variety of fermentation techniques are known in the art which may be employed in processes of the invention drawn to the production of amino acids.

Illustrative examples of suitable carbon sources include, but are not limited to: carbohydrates, such as glucose, fructose, sucrose, starch hydrulysate, cellulose hydrolysate and molasses; organic acids, such as acetic acid, propionic acid, formic acid, malic acid, citric acid, and fumaric acid; and alcohols, such as glycerol.

Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing, including meat extract, peptone, corn steep liquor, casein hydrolysate, soybean cake hydrolysate and yeast extract.

Generally, amino acids may be commercially produced from the invention in fermentation processes such as the batch type or of the fed-batch type. In batch type fermentations, all nutrients are added at the beginning of the fermentation. In fed-batch or extended fed-batch type fermentations one or a number of nutrients are continuously supplied to the culture, right from the beginning of the fermentation or after the culture has reached a certain age, or when the nutrient(s) which are fed were exhausted from the culture fluid. A variant of the extended batch of fed-batch, type fermentation is the repeated fed-batch or fill-and-draw fermentation, where part of the contents of the fermenter is removed at some time, for instance when the fermenter is full, while feeding of a nutrient is continued. In this way a fermentation can be extended for a longer time.

Another type of fermentation, the continuous fermentation or chemostat culture, uses continuous feeding of a complete medium, while culture fluid is continuously or semi-continuously withdrawn in such a way that the volume of the broth in the fermenter remains approximately constant. A continuous fermentation can in principle be maintained for an infinite time.

In a batch fermentation an organism grows until one of the essential nutrients in the medium becomes exhausted, or until fermentation conditions become unfavorable (e.g. the pH decreases to a value inhibitory for microbial growth). In fed-batch fermentations measures are normally taken to maintain favorable growth conditions, e.g. by using pH control, and exhaustion of one or more essential nutrients is prevented by feeding these nutrient(s) to the culture. The microorganism will continue to grow, at a growth rate dictated by the rate of nutrient feed. Generally a single nutrient, very often the carbon source, will become limiting for growth. The same principle applies for a continuous fermentation, usually one nutrient in the medium feed is limiting, all other nutrients are in excess. The limiting nutrient will be present in the culture fluid at a very low concentration, often unmeasurably low. Different types of nutrient limitation can be employed. Carbon source limitation is most often used. Other examples are limitation by the nitrogen source, limitation by oxygen, limitation by a specific nutrient such as a vitamin or an amino acid (in case the microorganism is auxotrophic for such a compound), limitation by sulphur and limitation by phosphorous.

The amino acid may be recovered by any method known in the art. Exemplary procedures are provided in the following: Van Walsem, H. J. & Thompson, M. C., *J. Biotechnol.* 59: 127-132 (1997), and U.S. Pat. No. 3,565,951, both of which are incorporated herein by reference.

All patents and publications referred to herein are expressly incorporated by reference.

EXAMPLES

Example 1

Chemical Mutagenesis and Selection of Valine Auxotrophs

A lysine producing *Corynebacterium* strain BF 100 was mutagenized with an alkylating agent as described in Miller, J. H. 1972 (Miller, J. H. 1972 *Experiments in Molecular Genetics.* Cold Spring Harbor Laboratory). Colonies were replica plated onto minimal medium (MM). Those that did not grow on MM but grew on complete medium (CM) were identified as auxotrophs. Those auxotrophs that were capable of growth on MM when supplemented with L-valine and L-isoleucine were selected for lysine yield analysis.

MM consisted of 20 g D-glucose, 10 g ammonium sulfate, 2.5 g urea, 1 g KH2PO4, 0.4 g MgSO4.7H20, 1 g NaCl, 0.01 g MnSO4.H20, 0.01 g FeSO4.7H20, 10 mg pantothenate, 50 mg biotin, 200 mg thiamine, and 50 mg niacinamide per liter at pH 7.2. When L-amino acids were used to supplement MM, 50 mg/L of each was used. MMIV was MM with isoleucine and valine added.

The growth pattern of a parent strain and a high yield-derivative produced by chemical mutagenesis on minimal agar plates supplemented with three amino acids is presented in Table 1. Supplements are at 50 mg/L L-amino acids. Growth is presented as relative colony size after 3 days at 30 C.

Example 2

Production of Branched Chain Auxotrophs with rDNA Technology

1. Preparation of a Deleted ilvB Gene

The ilvBN operon of *Corynebacterium* lactofermentum (ATCC 21799) was amplified by PCR and cloned into pCR-Script to make pAL203. The ilvB gene contains a 390 bp region separated by 2 EcoNI restriction sites. EcoNI does not cut the plasmid pCR-Script. The ilvB deletion allele was designed by cutting the plasmid pAL203 with EcoNI followed by selfligation to yield pAL203delta.

2. Homologous Recombination of a Modified ilvBN Allele into the *Corynebacterium* Chromosome A vector for allele exchange by double crossover was constructed as described by Maloy et al. 1996 (Maloy S. R., Stewart V. J., and Taylor R. K. 1996 *Genetic Analysis of Pathogenic Bacteria: A Laboratory Manual*, Cold Spring Harbor Press). ATCC 37766 was the source of pK184 a plasmid that replicates in *E. coli* but not in *Corynebacterium*. A sacB gene was subcloned into its SspI site to give pJC3. pJC3 cannot replicate in *Corynebacterium*. Any kanamycin resistant colonies will have the vector integrated into the chromosome by homologous recombination at a site within the cloned gene. Lethal expression of the sacB gene on the integrated vector prevents growth in the presence of sucrose. Growth in the presence of sucrose requires a second cross over to occur along an homologous region of the cloned insert. If the first and second crossovers flank a modification (deletion, site mutation), then the modified allele of ilvBN will be exchanged for the allele present on the chromosome of the host strain.

The modified allele of the ilvBN operon from pAL203Δ was subcloned into the integration vector pJC3 and electroporated into the BF100 strain of *Corynebacterium* and plated on rich medium plates lacking sucrose but having kanamycin (DMK). Colonies were picked and grown in rich broth lacking sucrose and kanamycin for 48 hrs. Cultures were streaked onto rich plates lacking kanamycin but having sucrose. Single colonies were picked from sucrose plates and replica plated on DMK, SM1, MM and MMIV. Strains that had no kanamycin resistance, could grow on sucrose, and could not grow on MM but could grow on MMIV were selected for shake flask experiments. LC10 is a BF 100-derived auxotroph.

The growth pattern of a parent strain and a high yield-derivative produced with recombinant DNA methods on a series of minimal agar plates supplemented with three amino acids is presented in Table 2. Supplements are at 50 mg/L L-amino acids. Growth is presented as relative colony size after 3 days at 30 C.

Example 3

Shake Flask Determination of L-Lysine Yield from Valine Auxotroph Strain Produced by Random Chemical Mutagenesis B4B inoculum was prepared by picking a single colony from an S1 plate and transferring to S1 broth. S1 was made by combining 50 g sucrose, 3 g K2HP04, 3 g urea, 0.5 g MgSO4.7H20, 20 g polypeptone, 5 g beef extract, 0.9 mg D-biotin, 3 mg thiamine, 125 mg niacinamide, 0.5 g L-methionine, 0.25 g L-threonine, 0.5 g L alanine per liter of water and adjusting the pH to 7.3. Plates included 20 g/L agar. After 16 hr growth of cultures in S1 broth, an equal volume of 30% glycerol was added and cultures were frozen at −80 C.

Baffled 250 mL seed shake flasks with 20 mL of SFM were inoculated with 0.1 mL of thawed inoculum. Seed medium (SFM) consisted of 60 g D-glucose, 3 g K2HP04, 3 g urea, 0.5 g MgSO4.7H20, 20 g polypeptone, 5 g beef extract, 3 mg D-biotin, 125 mg niacinamide, 0.5 g L-methionine, 0.25 g L threonine, and 0.5 g L-alanine per liter of water with pH adjusted to 7.3. Cultures were grown at 30 C for 16 hrs and aerated at 240 rpm with a 2 inch displacement. Two mL of seed culture was used to inoculate 21 mL of fermentation medium (FM4). FM4 medium was made by mixing 16 mL of main medium with 5 mL of dextrose stock. Dextrose stock was 180 g D-glucose plus 500 mL water. Main medium contained 0.083 g MnSO4, 0.4 mg D-biotin, cornsteep liquor, raffinate and 50 g CaC03 per liter. Cornsteep was added so that the final volume of FM4 was 4% dry solids. Raffinate was added so that the final volume of FM4 had 5% ammonium sulfate. Cultures were grown for 48 hrs at 30 C in 250 mL baffled shake flasks and aerated at 240 rpms with a 2 inch displacement.

Table 3 presents data on the production of L-lysine in shake flasks by *Corynebacterium* strain improved by selection for valine and isoleucine requirement.

Example 4

Shake Flask Determination of L-Lysine Yield from Valine Auxotroph Strain Produced by rDNA Methodology Table 4 presents data on the production of L-lysine in shake flasks by *Corynebacterium* strains improved by deleting 390 bases of DNA sequence from the chromosomal copy of the ilvBN operon (see Example 2). Cultures were grown and analyzed as described in Example 3.

Example 5

Microfermenation Determination of Lysine Yield by Valine Auxotroph

Inoculum was grown in 500 mL S1 in a 2 L baffled shake flask for 18 hrs. 3.1 L of FM4 medium was used in 4 L microfermentors. Temperature and pH were maintained at 32 C and 7.2, respectively. Agitation was increased from 700 rpms to 950 rpms at 20 hrs. Air was fed at 4.5 LPM. Dextrose was maintained at 3 g/L. Fermentation time was 48 hrs.

Table 5 presents data on the production of L-lysine in 4 liter fermentors using strains of *Corynebacterium* which cannot synthesize L-isoleucine and L-valine.

Example 6

L-Lysine Production by Bradytroph Produced by In Vivo Mutagenesis of Cloned IL VBN 1. Preparation of a Defective ilvBN Operon that Produces a Functional AHAS Enzyme The il vBN operon of pAL203 was subcloned into the shuttle vector pM2 to give pVAL1, pM2 can replicate in both *E. coli* and *Corynebacterium*. pVal1 was transformed into the mutagenic strain XL1RED from the Stratagene Co. Mutagenized plasmid was prepared according to the XL1RED kit instructions and electroporated into a valine auxotroph, *Corynebacterium*. A valine auxotroph is unable to grow on MM plates without supplementation by isoleucine and valine or genetic complementation with a functional ilvBN operon.

Kanamycin resistant transformants were selected from S1 plates and replica plated on to MM plates. Those colonies that grew on MM plates showed functional complementation of the ilvB deletion. Colonies that were smaller than the colonies of the valine auxotroph with the parent plasmid (pVAL1) were selected for the valine auxotroph activity assays, pRV1B5 is a plasmid derived from pVAL1 that can replicate in *E. coli* and *Corynebacterium*. In the valine auxotroph strain, it produced AHAS activity at less than 1% of the specific activity of AHAS produced by pVAL1. The ilvBN operon of this construct has leaky AHAS activity.

2. Homologous Recombination into *Corynebacterium* Chromosomal DNA

The RV1B5 leaky allele of the ilvBN operon was subcloned into the integration vector pJC3 and used to exchange the leaky allele for the deletion allele in a valine auxotroph by homologous recombination as done in Example 2. BF100-1030 is a valine bradytroph constructed with the RV1B5 allele. Table 6 presents data showing that BF100-1030 makes less valine in shake flasks than its parent strain. Table 7 shows that BF100-1030 bradytroph has improved growth over the auxotrophs in Table 5. Table 7 also shows that the bradytroph produces less valine in microfermentors than the parent strain.

TABLES

Data presented in the following tables are discussed in the Examples section. Note that the term "Growth" refers to the optical density measured at 660 nm; the term "Titre" refers to the grams of amino acid per liter; the term "Yield" is defined by the following formula: [(g lysine/L/(g dextrose consumed/L)]*100; B4B=a valine autotroph constructed with chemical mutagenesis; LC10=a valine autotroph constructed by replacing the chromosomal ilvB gene with the ilvB deletion allele of pAL203 A; BF 100-1030=a valine bradytroph constructed by replacing the chromosomal ilvB gene with the RV1B5 leaky allele.

TABLE 1

Valine Auxotroph Selection Following Chemical Mutagenesis

| Agar Plate | Amino Acid Supplement | | | Relative Growth | |
| --- | --- | --- | --- | --- | --- |
| | ile | leu | val | BF100 | B4B |
| MM | − | − | − | 5 | 0 |
| MM | + | + | − | 5 | 0 |
| MM | + | − | − | 5 | 2 |
| MM | − | + | + | 5 | 0 |
| MM | + | + | + | 5 | 5 |

TABLE 2

Auxotroph Selection Following rDNA Modification

| Agar Plate | Amino Acid Supplement | | | Relative Growth | |
| --- | --- | --- | --- | --- | --- |
| | ile | leu | val | BF100 | LC10 |
| MM | − | − | − | 3 | 0 |
| MM | + | + | − | 3 | 0 |
| MM | + | − | + | 3 | 1 |
| MM | − | + | + | 3 | 0 |
| MM | + | + | + | 3 | 3 |

TABLE 3

Shake Flask Determination of L-lysine Yield From a Valine Auxotroph Strain Produced by Random Chemical Mutagenesos

| Strain | Growth | Lysine Titre | % Yield |
| --- | --- | --- | --- |
| Parent-1 | 33 | 18 | 32 |
| B4B | 33 | 17 | 44 |

TABLE 4

Shake Flask Determination of L-lysine Yield From a Valine Auxotroph Strain Produced by rDNA Methodology

| Strain | Growth | Lysine Titre | % Yield |
|---|---|---|---|
| BF100 | 35 | 25 | 38 |
| LC10 | 35 | 28 | 43 |

TABLE 5

Microfermenation Determination of Lysine Yield

| Strain | Growth | Lysine Titre | % Yield | Valine Titre |
|---|---|---|---|---|
| BF100 | 90 | 113 | 37 | 8.9 |
| LC10 | 63 | 86 | 50 | 1.1 |
| B4B | 70 | 91 | 51 | — |

TABLE 6

Shake Flask Determination of Decreased L-Valine Titre from a Valine Bradytroph Strain Produced by Integrating the RV1B5 allele of ilvB into the Chromosome

| Strain | Growth | Lysine Titre | % Yield | Valine Titre |
|---|---|---|---|---|
| BF100 | 36 | 27 | 29 | 5.2 |
| BF100-1030 | 42 | 22 | 25 | 3.5 |

TABLE 7

Microfermentation Determination of Decreased L-Valine Titre from a Valine Bradytroph Strain Produced by Integrating the RV1B5 Allele of ilvV into the Chromosome

| Strain | Growth | Lysine Titre | % Yield | Valine Titre |
|---|---|---|---|---|
| BF100 | 89 | 134 | 43 | 9 |
| BF100-1030 | 78 | 123 | 44 | 6 |

What is claimed is:

1. A method of making a microorganism that produces amino acid X comprising:
   (a) selecting a parental population of microorganisms A that contain an ilvBN operon and produce said amino acid from dextrose in percent yield Y;
   (b) mutagenizing said parental population of microorganisms A to produce a population of mutagenized microorganisms B;
   (c) selecting from the population of mutagenized microorganisms B, at least one mutagenized microorganism C that has at least one of a deletion, an insertion, and a point mutation in said ilvBN operon and that produces said amino acid X from dextrose in percent yield Z, wherein said percent yield Z is greater than said percent yield Y, and wherein said amino acid X is selected from the group consisting of L-lysine, L-threonine, L-methionine, and homoserine.

2. The method of claim 1, wherein said parental population of microorganisms A is mutagenized by random chemical mutagenesis.

3. The method of claim 2, wherein said microorganism C comprises an endogenous ilvBN operon.

4. The method of claim 1, wherein microorganism A is mutagenized by rDNA mutagenesis of the ilvBN operon of microorganism A.

5. The method of claim 4, wherein the mutagenesis is the result of a transformation with a vector comprising a recombinant polynucleotide comprising SEQ ID NO: 5.

6. The method of claim 1, wherein said mutagenized microorganism C is bradytrophic for valine.

7. The method of claim 6, wherein said mutagenized microorganism C is bradytrophic for valine and isoleucine.

8. The method of claim 6, wherein said mutagenized microorganism C is bradytrophic for valine and leucine.

9. The method of claim 8, wherein said mutagenized microorganism C is bradytrophic for valine, leucine, and isoleucine.

10. The method of claim 1, wherein said parental microorganism A, said microorganism B, and said mutagenized microorganism C are strains of *Corynebacterium*.

\* \* \* \* \*